US 11,816,815 B2

(12) United States Patent
Hariharan et al.

(10) Patent No.: US 11,816,815 B2
(45) Date of Patent: Nov. 14, 2023

(54) COMPUTER-IMPLEMENTED METHODS AND SYSTEMS FOR PROVISION OF A CORRECTION ALGORITHM FOR AN X-RAY IMAGE AND FOR CORRECTION OF AN X-RAY IMAGE, X-RAY FACILITY, COMPUTER PROGRAM, AND ELECTRONICALLY READABLE DATA MEDIUM

(71) Applicant: Siemens Healthcare GmbH, Erlangen (DE)

(72) Inventors: Sai Gokul Hariharan, Forchheim (DE); Heiko Rohdjeß, Grossenseebach (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 17/845,968

(22) Filed: Jun. 21, 2022

(65) Prior Publication Data
US 2022/0405897 A1 Dec. 22, 2022

(30) Foreign Application Priority Data
Jun. 22, 2021 (DE) ...................... 10 2021 206 417.5

(51) Int. Cl.
*G06T 5/00* (2006.01)
*A61B 6/00* (2006.01)
(Continued)

(52) U.S. Cl.
CPC ............ *G06T 5/006* (2013.01); *A61B 6/4035* (2013.01); *A61B 6/52* (2013.01); *G06T 5/002* (2013.01);
(Continued)

(58) Field of Classification Search
CPC .......... G06T 5/006; G06T 5/002; G06T 5/20; G06T 9/002; G06T 2207/10116;
(Continued)

(56) References Cited

U.S. PATENT DOCUMENTS 6,570,951 B1 5/2003 Hsieh
9,820,715 B2* 11/2017 Kang .................. A61B 6/4035
(Continued)

FOREIGN PATENT DOCUMENTS

DE 102019215242 A1 4/2021

OTHER PUBLICATIONS

Wang, Dayang, et al. "Masked Autoencoders for Low dose CT denoising." arXiv preprint arXiv:2210.04944 (2022). (Year: 2022).*
(Continued)

*Primary Examiner* — Andrae S Allison
(74) *Attorney, Agent, or Firm* — Lempia Summerfield Katz LLC

(57) ABSTRACT

A computer-implemented method for provision of a correction algorithm for an x-ray image that was recorded with an x-ray source emitting an x-ray radiation field, a filter facility spatially modulating an x-ray radiation dose, and an x-ray detector is provided. The correction algorithm includes a trained first processing function that, from first input data that includes at least one first physical parameter describing the x-ray radiation field and/or the measurement and at least one second physical parameter describing the spatial modulation of the filter facility, determines first output data. The first output data includes a mask for brightness compensation with regard to the spatial modulation of the filter facility in the x-ray image. The method includes providing first training data, providing an autoencoder for masks, and training of the autoencoder using the first training data. The
(Continued)

method also includes determining an assignment rule, and providing the trained first processing function.

15 Claims, 9 Drawing Sheets

(51) Int. Cl.
  *G06T 5/20* (2006.01)
  *G06T 9/00* (2006.01)
(52) U.S. Cl.
  CPC .............. *G06T 5/20* (2013.01); *G06T 9/002* (2013.01); *G06T 2207/10116* (2013.01); *G06T 2207/20081* (2013.01); *G06T 2207/20084* (2013.01)
(58) Field of Classification Search
  CPC . G06T 2207/20081; G06T 2207/20084; G06T 5/007; A61B 6/4035; A61B 6/52; G06N 3/0455; G06N 3/0464; G06N 3/0475; G06N 3/084; G06N 3/088
  See application file for complete search history.

(56) References Cited

U.S. PATENT DOCUMENTS

| | | | |
|---|---|---|---|
| 2014/0198131 | A1 | 7/2014 | Rudin et al. |
| 2016/0206274 | A1* | 7/2016 | Kang .................... A61B 6/4035 |
| 2017/0296131 | A1 | 10/2017 | Bernhardt et al. |
| 2018/0168524 | A1 | 6/2018 | Melman |
| 2018/0330233 | A1 | 11/2018 | Rui et al. |
| 2019/0080490 | A1* | 3/2019 | Schoendube ......... G06T 11/005 |
| 2019/0216409 | A1 | 7/2019 | Zhou et al. |
| 2020/0196972 | A1 | 6/2020 | Zhou et al. |
| 2021/0093286 | A1* | 4/2021 | Stierstorfer ............. G01T 7/005 |
| 2023/0083134 | A1* | 3/2023 | Regensburger ....... G06T 11/008 250/363.03 |
| 2023/0085938 | A1* | 3/2023 | He .......................... G06N 3/045 706/20 |
| 2023/0090743 | A1* | 3/2023 | Pinto .................... G06V 10/454 382/141 |

OTHER PUBLICATIONS

Chatterjee1 et al., Variational Autoencoder Based Imbalanced COVID-19 Detection Using Chest X-Ray Images, New Generation Computing (2023) 41:25-60 (Year: 2023).*
Setlur Nagesh et al., "Image processing using Convolutional Neural Network (CNN) for Region of Interest (ROI) fluoroscopy," Proc. SPIE 11317, Medical Imaging 2020: Biomedical Applications in Molecular, Structural, and Functional Imaging, 1131718 (Feb. 28, 2020); doi: 10.1117/12.2549242 (Year: 2020).*
Li, Bo, et al. "Denoising convolutional autoencoder based B-mode ultrasound tongue image feature extraction." ICASSP 2019-2019 IEEE International Conference on Acoustics, Speech and Signal Processing (ICASSP). IEEE, 2019. (Year: 2019).*
Decision to Grant for German Application No. 10 2021 206 417.5 granted Jun. 30, 2022, with English translation.
German Office Action for German Application No. 10 2021 206 417.5 dated Apr. 1, 2022, with English translation.
German Office Action for German Application No. 10 2021 206 417.5 dated Mar. 21, 2022, with English translation.
Isola, Phillip, et al. "Image-to-image translation with conditional adversarial networks." Proceedings of the IEEE conference on computer vision and pattern recognition. 2017. pp. 1-17.
Nagesh, SV Setlur, D. R. Bednarek, and S. Rudin. "Estimation of attenuator mask from region of interest (ROI) dose-reduced images for brightness equalization using convolutional neural networks." Medical Imaging 2019: Physics of Medical Imaging. vol. 10948. SPIE, 2019.
Nagesh, SV Setlur, et al. "Image processing using Convolutional Neural Network (CNN) for Region of Interest (ROI) fluoroscopy." Medical Imaging 2020: Biomedical Applications in Molecular, Structural, and Functional Imaging. vol. 11317. SPIE, 2020.
Schafer, Sebastian, et al. "Filtered region of interest cone-beam rotational angiography." Medical physics 37.2 (2010): 394-703.

* cited by examiner

COMPUTER-IMPLEMENTED METHODS AND SYSTEMS FOR PROVISION OF A CORRECTION ALGORITHM FOR AN X-RAY IMAGE AND FOR CORRECTION OF AN X-RAY IMAGE, X-RAY FACILITY, COMPUTER PROGRAM, AND ELECTRONICALLY READABLE DATA MEDIUM

This application claims the benefit of DE 10 2021 206 417.5, filed on Jun. 22, 2021, which is hereby incorporated by reference in its entirety.

BACKGROUND

The present embodiments relate to provision of a correction algorithm for an x-ray image that was recorded with an x-ray source emitting an x-ray radiation field, a filter facility spatially modulating the x-ray radiation dose in the x-ray radiation, and an x-ray detector.

In medical interventions (e.g., minimally invasive interventions), it is known that the interventions may be carried out under imaging control, in order, for example, to be able to observe the position of a medical instrument (e.g., a catheter) relative to the anatomy and/or also to be able to see changes in the anatomy. For various reasons, x-ray imaging is frequently employed in the prior art in such cases, so that, for example, fluoroscopy images may be recorded using an x-ray facility with a C-arm that is able to be brought into different positions relative to the patient. Despite this, with such an x-ray facility, there remains sufficient space for medical personnel who are carrying out and/or monitoring the intervention.

A disadvantage of x-ray imaging, however, is the radiation load that occurs. Thus, during x-ray-guided medical procedures, both the patient and also the medical personnel involved are subjected over time to a certain, in some cases not inconsiderable, dose of x-ray radiation. In order to reduce this x-ray dose and thus also the risk of health consequences possibly correlated therewith, the dose for the patient is to be optimized and the dose for the medical personnel is to be minimized. This is frequently expressed as the ALARA principle, wherein the acronym stands for "As Low As Reasonably Achievable". This provides that the x-ray dose should be as low as possible while maintaining the necessary image quality.

A variant known in the prior art for reducing the x-ray load provides for the use of a filter facility spatially modulating the x-ray radiation dose, especially an ROI filter, in order to keep the image quality for the highly relevant region (e.g., the Region of Interest (ROI)) high, but still be able to provide the surrounding anatomy context at a lower image quality. An ROI filter is a semi-transparent filter facility that, for a region not essentially attenuating the x-ray radiation (e.g., a passage opening in the x-ray radiation field) allows a standard x-ray dose to be provided, while outside this ROI, a filter material provides that a markedly lower x-ray dose is present. The outer region of the ROI filter surrounding the ROI may, for example, consist of a thin layer of a material strongly absorbing x-ray radiation, such as tungsten or lead. For example, filter faculties have been proposed that use a layer of tungsten 0.127 mm thick.

When such a filter facility spatially modulating the x-ray radiation dose is used, a reduction in the brightness also occurs as a consequence wherever the x-ray dose is reduced. In this context, to provide a uniform image impression, it is proposed that a brightness correction (e.g., using an additive brightness correction mask) be used in order to standardize the brightness over the x-ray image to be corrected (e.g., after application of an algorithmic transformation). However, determining such a mask has proved not to be trivial, since the mask depends on a plurality of different factors, such as, for example, on settings of the x-ray source (e.g., of an x-ray tube), x-ray detector settings, pre-filtering measures (e.g., the use of copper), location and size of the ROI, the recorded object, and the jittering of the focus point (e.g., due to the electromagnetic field of the tube drive).

An example of an embodiment of an ROI filter is described by US 2018/0168524 A1. In the document, a number of stacked exchangeable filters are fastened in a housing in an x-ray facility. Each filter includes an ROI opening. In this case, the ROI openings and thus the ROIs of at least two of the filters differ. However, other options have also already been proposed for adapting the ROI of such an ROI filter (e.g., by a system of actuators) that shifts the ROI. A temporal change in the spatial modulation of a filter facility may be based on a user input, but may also be undertaken (e.g., in real time) by adjusting the view.

With respect to the determination of a brightness correction, mask model-based approaches have been proposed, for example, in order to estimate the masks. The model uses parameters such as tube settings, geometry values, and filter settings. Due to the great complexity of the problem, such model approaches have, however, not proved to be of any great value. Therefore, there is also an approach for deriving masks for brightness adaptation from a calibration measurement (e.g., by using images that were recorded without an object ("flat-field images")). In such cases, an x-ray image is recorded with a filter facility, after which a further x-ray image is recorded with same system settings, but without the use of the filter facility, however. Then, a brightness correction mask may be derived from the x-ray images by subtracting the x-ray image recorded with the filter facility from the x-ray image recorded without the filter facility.

In such calibration measurements, it has been established for an ROI filter that the values within the ROI in the mask essentially amount to zero, and in the outer region, the values lie at an essentially constant higher value. A smooth transition between the values within the ROI and outside the ROI has, however, been established. This creates the impression that a model-based correction for deriving a brightness correction mask would have to be conceivable; it has also been determined, however, that the shape of the ROI in the mask deviates from the shape of the ROI at the ROI filter. For example, the mapping of the ROI in the mask is not circular, although this is true for the ROI of the filter facility. This may have different causes (e.g., the jittering of the focus point of the x-ray source and/or the location of the physical ROI filter in relation to the x-ray radiation field).

The derivation of a brightness correction mask has proved to be even more difficult in the presence of the object to be imaged (e.g., of a patient). In addition to the factors already mentioned (e.g., a jittering focus point and the arrangement of the physical ROI filter in the x-ray radiation field), stray radiation, beam hardening, and heel effects arise here, which likewise play a significant role. Thus, the use of a model-based approach dependent of various system parameters mostly proves to be inadequate for compensating for the brightness in the x-ray image (e.g., in the transition area from the ROI to the outer region).

One possible approach has been proposed in an article by S. Schafer et al., "Filtered region of interest cone-beam rotational angiography," Medical Physics 37 (2010), pages 694-703. In this approach, the pixels in the transition area are reconstructed using complicated interpolation-based approaches. These approaches, however, often prove to be not adequate enough, too complicated in robust implementation, and unsuitable for use in real time, which, however, is of significance for the monitoring of medical interventions.

SUMMARY AND DESCRIPTION

The scope of the present invention is defined solely by the appended claims and is not affected to any degree by the statements within this summary.

The present embodiments may obviate one or more of the drawbacks or limitations in the related art. For example, an improved option for brightness correction in x-ray images recorded with a filter facility spatially modulating an x-ray dose in an x-ray radiation field (e.g., an ROI filter) that, for example, brings a high image quality and real time capability is provided.

In a computer-implemented method for providing a correction algorithm for an x-ray image that was recorded with an x-ray source emitting an x-ray radiation field, a filter facility spatially modulating the x-ray radiation dose in the x-ray radiation field (e.g., an ROI filter), and an x-ray detector, there is provision in accordance with the present embodiments for the correction algorithm to include a trained first processing function. The trained first processing function, from first input data, which includes at least one first physical parameter describing the x-ray radiation field and/or the measurement and at least one second physical parameter describing the spatial modulation of the filter facility, determines first output data. The first output data includes a mask for brightness compensation with regard to the spatial modulation of the filter facility in the x-ray image. The method includes providing first training data including first training datasets each with a mask. Each first training dataset is assigned the first and second physical parameters of the first input data assigned for determining the mask. The method includes providing an autoencoder for masks. The autoencoder has an encoder for determining a latent space representation of the mask and a decoder for determining a comparison mask from the latent space representation. The method includes training of the autoencoder using the first training data. The method includes determining an assignment rule between the physical parameters of the first input data that are assigned to the first training datasets, and the latent space representations of the masks of the first training dataset in each case. The method includes providing the trained first processing function as a combination of the assignment rule and the trained decoder.

This first method of the present embodiments may thus be a provision method (or also training method) for providing a correction algorithm that makes improved brightness correction possible. In this case, the solution are described below both with respect to provision methods and systems and also of correction methods and systems, an x-ray facility, as well as corresponding computer programs and/or electronically readable data media. Features, advantages, or forms of embodiment may be transferred in this case between the different subject matter. In other words, this provides that methods and systems for the provision may be improved by features that are described in the context of methods and systems for correction, and vice versa.

The present embodiments employ artificial intelligence in the form of trained processing functions. In general, a trained function, which may also be referred to as an algorithm of artificial intelligence, maps cognitive functions that are associated with the functioning of the human mind. Through training based on training data, the trained function is in a position to adapt to new circumstances and to detect and to extrapolate patterns.

Generally, parameters of a trained function may be adapted by training. For example, supervised training, semi-supervised training, unsupervised training, reinforcement learning, and/or active learning may be used. Within the framework of the present embodiments, for example, representation learning (e.g., feature learning) is employed for the first processing function. Generally, the parameters of a trained function may be adapted iteratively by a number of training steps.

A trained function may, for example, include a neural network, a Support Vector Machine (SVM), a decision tree, and/or A Bayesian network, and/or a die trained function may be based on k-means clustering, Q learning, genetic algorithms, and/or assignment rules. For example, a neural network may be a deep neural network, a convolutional neural network (CNN), or a deep CNN. A neural network may further be an adversarial network, a deep adversarial network, and/or a generative adversarial network (GAN). Within the framework of the present embodiments, trained processing functions, for example, include at least one CNN.

The aim of the provision method is to provide a correction algorithm that determines, from input data of the correction algorithm, a mask that makes possible a brightness compensation in an x-ray image to be corrected in real time and with an image quality that is as artifact-free as possible. The mask thus involves a brightness correction mask that may be applied additively.

To do this, the first basic provision is to train a first processing function based on training data masks that have been determined for different system settings, described by the first and the second physical parameters. In this case, it has been recognized that both first physical parameters, which relate to the system settings of the x-ray facilities in general (e.g., the creation of the x-ray radiation), the recording geometry, and the detector settings), and also second physical parameters, which describe the filter facility and its current state, should be used. In such cases, the first and second physical parameters may cover at least the system settings that are seen as essential in their influence on the different brightness in the x-ray image to be corrected.

The mask images of the first training data are now used to train an autoencoder (e.g., a convolutional autoencoder comprising a CNN). During this process, the encoder of the autoencoder is trained to describe the input mask by a minimal set of characteristics (e.g., a latent space representation). The decoder of the autoencoder is trained to use the characteristics encoded as latent space representation and to reconstruct the mask input. This provides that a comparison mask is obtained as output of the autoencoder, of which the difference to the mask input of the first training data is minimized.

The idea underlying the further procedure is that now, for the most precise possible reconstruction of the mask from the latent space representation (e.g., the minimal set of characteristics), similar masks should have a similar latent space representation. In other words, masks that differ due to a change in one of the physical parameters, which actually represent system settings/recording parameters, have a comparable latent space representation in the latent space. A number of differences in the latent space parameters occur that relate to the characteristics that relate to the corresponding first or second physical parameters. If, for example, the mapping geometry regarding the ROI changes (e.g., this is mapped with changes), differences occur in the latent space parameters of the latent space representation that describe the location of the ROI in the mask.

If the first and second physical parameters of the first training data now cover a possible region of interest of first and second physical parameters that may be set, the relationship between the physical parameters and the associated latent space representations described by an assignment rule may be generalized starting from the measurement points present through the training datasets (e.g., by fitting and/or interpolation and/or extrapolation). Thus, through the assignment rule, latent space representations may also be determined for sets of first and second physical parameters that were not contained in the first training data. The trained decoder supplies the corresponding mask for this.

Thus, the first processing function consists of a combination of the assignment rule and the decoder and, as first input data for different sets of first and second physical parameters describing system settings, delivers a suitable mask for these system settings.

This method of operation brings with it a plurality of advantages. An approach based on machine learning, which is based on x-ray physics, is provided to reduce artifacts through the use of a filter facility that modulates the x-ray radiation dose spatially and thus to improve the image quality. Through the correction algorithm, a workflow able to be carried out in real time for analysis and correction of artifacts due to the filter facility is provided. In this case, the proposed physics-driven approach makes possible representation learning and the interpolation of the latent space parameters learned, so that the necessity of recording an unmanageable plurality of calibration images at different system settings is also avoided in order to determine suitable mask images. In this way, the time for an exhausting calibration of different x-ray facilities is saved and yet an effective correction is still provided.

In one embodiment, there may be provision for a greater number of latent space parameters of the latent space representation to be used as physical parameters of the first input data. In specific terms, for example, 3 to 30 physical parameters of the first input data and/or 3 to 30 latent space parameters of the latent space representation may be used. The use of a greater number of latent space parameters as physical parameters brings with it the advantage that ultimately an overdetermination is present, which makes possible the determination of the assignment rule in an especially reliable way. For example, when four first and second physical parameters are used, ten latent space parameters of the latent space representation are used; when ten first and second physical parameters are used, twenty-five latent space parameters are used. Other embodiments may also be provided.

In one embodiment, the determination of the at least one functional relationship (e.g., an assignment rule exclusively containing functional relationships) may take place at least partly by fitting and/or by interpolation and/or by extrapolation. This provides that the assignment rule is kept as simple as possible, so that the assignment rule may be implemented in an uncomplicated manner (e.g., with respect to the real time capability in a corresponding correction system). It has been shown in such cases that simple functional relationships are actually entirely sufficient, which may then be parameterized for determining the assignment rule accordingly through techniques of fitting, of interpolation, and/or of extrapolation. This provides that, in exemplary embodiments, artificial intelligence itself is not used for the assignment rule.

A plurality of options exists for the actual choice of the first and second physical parameters. In such cases, the first physical parameter in each case may at least include one first physical parameter from a subgroup in each case. The subgroups include a subgroup with first physical parameters related to the creation and/or modification of the x-ray radiation, a subgroup with first physical parameters related to the recording geometry, and a subgroup with first physical recording parameters related to the measurement (e.g., by the x-ray detector). Optionally, a jittering of the focus point of the x-ray source, which is then, for example, embodied as the x-ray tube, may also be mapped by the first physical parameters. This effect is frequently also designated as wobbling in relation to the filter facility. For example, when a second processing function is also used in the correction algorithm, which will be discussed in greater detail below, effects related to the jittering of the focus point may also be taken into account by this.

In a specific development of the present embodiments, there may, for example, be provision for the first physical parameters to be selected from the group comprising: A tube voltage of the x-ray source; a tube current of the x-ray source; a pre-filter parameter and/or an aperture parameter; a distance of the x-ray source to the x-ray detector; a distance of the x-ray source to the filter facility; a distance of the filter facility from the x-ray detector; a pulse length of the x-ray pulse creating the x-ray radiation field; a number of x-ray pulses since the beginning of the recording of a series of x-ray images; at least one focal parameter describing the geometry of the focus point; a zoom of the x-ray detector; an orientation of the x-ray detector; and a frame rate of the x-ray detector. Alternatively or additionally, the second physical parameters are selected from the group comprising: A material of the filter facility; at least one filter thickness parameter (e.g., describing the course of a filter thickness); and at least one time parameter describing a change over time of the spatial modulation.

Parameters for creating the x-ray radiation or for influencing the x-ray radiation before the x-ray radiation reaches the filter facility (e.g., a tube voltage, a tube current, a pre-filter parameter, and/or an aperture parameter) thus, for example, describe the strength and also the shape of the x-ray radiation field that arises (e.g., the presence of a fan beam or cone beam geometry as well as the basic x-ray dose or its distribution). All these system settings ultimately give indications of what would have been measured at the x-ray detector if no filter facility were present. This, however, may also be relevant for the filter effect of the filter facility itself. Also important here is the recording geometry (e.g., also already in relation to the filter facility as object), since it is a matter of the completion of the mapping of the spatially modulating filter facility at the x-ray detector. Variables known and also useful within the framework of the present embodiments in this regard include the distance of the x-ray source to the x-ray detector, often also referred to as the source image distance (SID), the distance of the x-ray source to the filter facility, which forms the object (e.g., often also referred to as the source object distance (SOD)), and the distance of the filter facility from the x-ray detector (e.g., object image distance (OID)). In this case, it is already sufficient for two of these parameters to be known, since the third follows from them.

Effects of the jittering of the focus point may also be important. This may arise, for example, due to electromagnetic fields. Since the filter facility is usually arranged relatively close to the focus point (e.g., at a distance of 3 to 10 cm, such as 5 cm), such small "jitter effects" of the "jittering" may be magnified to a "wobbling" of specific subregions of the filter facility (e.g., of an ROI). Since the jittering mostly follows a specific course of time after the start of the image recording, which for the monitoring of a medical intervention, relates to the recording of a plurality of individual x-ray images (e.g., frames) after one another, the pulse length of the x-ray pulse creating the x-ray radiation field and the number of x-ray pulses since the beginning of the recording of a series of x-ray images have proven to be a useful first physical parameter (e.g., exactly like a frame rate of the x-ray detector). If it is then known, for example, which number frame since the beginning of the recording of a current series of x-ray images is present, a deduction may be made about a current position of the jittering focus point or the wobbling ROI from a basically known movement sequence. In this case, it should be pointed out in general, since the starting point is frequently a pure point-form focus point, that relevant deviations herefrom (e.g., a focal parameter describing the geometry of the focus point) may likewise be taken into account. Further parameters of the x-ray detector (e.g., the zoom and/or an orientation of the x-ray detector) relate primarily to the existing recording geometry. However, a movement of the detector (e.g., a vibration or jittering there) may also occur and be described by first physical parameters.

With regard to the second physical parameters, as well as a second physical parameter describing an attenuation effect, reflecting a filter material of the filter facility, these may, for example, reflect the filter thickness course (e.g., current filter thickness course), for example, with reference to at least one filter thickness parameter. In one embodiment, the second physical parameters may also be a time parameter describing a change over time of the spatial modulation (e.g., when information about this is available, such as a new position for the ROI has just been moved to), which results from a user input and is undertaken with a specific speed profile, or which consists of a clearly predefined tracking task for a medical instrument (e.g., a catheter). Other effects able to be described by a time parameter may also be a "jittering" of the filter facility, (e.g., during operation of motors). Since with eye tracking it is rather difficult to make a prediction, there may be provision to postpone such effects to a further processing stage still to be discussed further below.

In one embodiment, the first training datasets may be determined from x-ray images recorded with and without filter facility (e.g., as flat-field x-ray images). Thus, the process that has frequently served to date as a calibration measurement may be used to create the first training data, in that recordings without patients (e.g., flat-field x-ray images) are made. The same system settings (e.g., the same first and second physical parameters) are used in each case. If (e.g., after the usual logarithmic transformation) the x-ray image with the filter facility is subtracted from the x-ray image without the filter facility, the corresponding mask for the training data is produced. In this context, a correction within the framework of the present embodiments may accordingly take place by addition of a mask to be used for correction to the x-ray image (e.g., logarithmically transformed image) to be corrected.

In an embodiment, the foundations for a two-stage procedure will be established by the correction algorithm, as well as the first processing algorithm, also including a second processing algorithm. Through this, a mask determined by the first processing algorithm from the first input data is to be refined with regard to other effects (e.g., as well as the system settings), and to be greatly improved again (e.g., also general conditions). In specific terms, in this type of embodiment, there is provision for the correction algorithm further to have a second processing function downstream of the first trained processing function for refining the mask determined by the first processing function. The second processing function has a generator network that uses as second input data an x-ray image for which the refined mask is to be determined, and a mask to be refined determined by the trained first processing function for the physical parameters of the second input data of the second input data. For training the second processing function, second training data including x-ray images of an object (e.g., of a patient) recorded with and without filter facility, with assigned physical parameters of the first input data, are provided, A discriminator network to discriminate between true x-ray images recorded without filter facility and corrected x-ray images obtained using the refined mask received as the second output data is provided to supplement a generative adversarial network (GAN), For training of the generator network and the discriminator network, an output of the discriminator network (e.g., an adversarial loss value) by comparing a corrected x-ray image of a second training dataset with the x-ray image of the second training dataset recorded without filter facility is used for fitting the generator network and the discriminator network. The correction algorithm including a combination of the trained first and the trained second processing function is provided.

This provides that, in the correction algorithm and thus also in the provision method, a two-stage process, in which representation learning is combined with a generative adversarial network in order to train a first processing function and a second processing function, is realized. The first processing function, as its basic assumption, provides a first estimation of the brightness correction mask (e.g., the mask to be refined) based on the system settings. This is then again greatly improved by the second processing algorithm (e.g., in order to take account of effects not able to be derived or unable to be derived directly from the system settings).

In this case, the actual x-ray image to be corrected may also be taken into consideration. The actual x-ray image to be corrected has brightness characteristics that are also attributable to the mapping effects of the filter facility, which may accordingly be extracted by a generator network for refining the mask to be refined. In other words, the estimate of the mask due to the current system settings is calculated by the decoder being applied to the latent space representation, which corresponds to the system settings. Based on the x-ray images recorded with the filter facility (e.g., after the application of a logarithmic transformation), the refinement is undertaken. The generator network in this case may use residual blocks, skip connections, downsampling layers, upsampling layers, and/or spatial transformation layers. A refined mask is then obtained as output, by which a corrected x-ray image (e.g., through addition of the mask to the x-ray image to be corrected of the second input data) may be determined. For training, this corrected x-ray image is compared by the discriminator network with an x-ray image present in the second training data, recorded without filter facility, since such an image may correspond to it. In this case, the x-ray images recorded with and without filter facility do not absolutely have to relate to the same object or the same conditions, since the discriminator as an adversarial system should be able to distinguish the quality as "with" and "without" filter facility effects. In other words, as is usual with a GAN, the generator attempts to "deceive" the discriminator and the latter attempts to "see through" the generator. The result of the discriminator is used in order to adapt the parameters of the generator network and of the discriminator network, as is known from GAN concepts, in an iteration step. This provides that "adversarial training" or adversary-based training is used by a discriminator network that is to discriminate between real images (e.g., in the absence of the filter facility) and corrected, calculated x-ray images being employed. The output of the discriminator network may be an adversarial loss value (e.g., an "adversarial loss" or "classification loss"). This output may be used for updating the generator network and the discriminator network. As soon as the training is concluded, the generator network used as a further processing function will be in a position to deliver refined masks, after the application of which for correction, corrected x-ray images are obtained that correspond extremely precisely to real x-ray images.

The second processing function may take account of effects that are not able to be derived or are only able to be derived with difficulty from the system settings. These effects may, for example, also be the "jittering" of the focus point due to electromagnetic fields due to the drive frequency of the stator of the x-ray source embodied as the x-ray tube. Over and above this, however, as well as such wobbling of regions given by the filter facility such as the ROI, further temporal, for example, difficult-to-predict effects are taken into account (e.g., a rapid change at the filter facility through eye tracking, such as an adjustment for example of an ROI in accordance with current view of a person conducting a medical intervention (eye tracking)). Also, the significant effects of an object to be recorded are taken into account (e.g., including beam hardening and/or scattered radiation effects). Thus, the addition of the second processing function again offers a marked improvement in the quality and robustness of the correction available through the correction algorithm.

This enables extremely realistic, artifact-free corrected x-ray images to be created, which allows a significant reduction of the x-ray dose, since even with low doses outstanding effects are obtained.

The present embodiments (e.g., in the embodiment with first and second processing function) also allow a reduction of the costs for the development and use of specific and expensive techniques for internal screening of different components within an x-ray tube as x-ray source. This is, for example, because the approach with the second processing function may potentially correct all sources of variation of the brightness, both technically and also specific to the patient, so that, for example, better results are provided for the same or even a lower development outlay.

The present embodiments make it possible to record x-ray images in the presence of a semi-transparent filter facility even with low pulse length, since, either by the first processing function and/or by the second processing function, artifacts will be corrected that arise through the jittering of the focus point. This, for example, also permits the use of dual-energy imaging with the use of a semi-transparent filter facility. Consecutive frames of the same scene are recorded at short intervals with different energy spectra, where extremely short pulse lengths are provided in order to guarantee the spatial mapping authenticity.

In one embodiment, there may be provision for the generator network, at least during its training, to receive as further second input data at least one boundary condition restricting its second output data. In specific terms, the at least one boundary condition may be chosen, for example, from the group including: A boundary condition restricting the deviation of the refined mask from the mask to be refined and/or the space of the possible mask to be refined; a boundary condition providing the smoothness of the refined mask; and a boundary condition restricting the type of the arithmetic operations to obtain the refined mask from the mask to be refined.

Boundary conditions may thus, for example, make sure that the refined mask belongs to the space of the masks that are determined by the first processing function, or at least approximates to the space extremely closely. Boundary conditions may further provide smoothness and only allow a specific set of arithmetical operations in order to get from the mask to be refined to the refined mask. In this way, it is possible, using physically motivated boundary conditions, to prevent the correction algorithm from generating unrealistic outputs, which may irritate medical personnel. Boundary conditions may also contribute to achieving a general brightness stabilization in the corrected x-ray image. Basically, the use and definition of boundary conditions is already known in the prior art, so that this does not have to be discussed in any greater detail here.

The proposed procedure, based on machine learning and driven by x-ray physics, thus uses boundary conditions that are derived from actual knowledge about the reality and the physics. This provides that the correction algorithm delivers masks and thus corrected x-ray images that are realistic and do not have any confusing artifacts.

As already mentioned, the x-ray images, as is usual in the prior art, before their use (e.g., as training data and/or input data), are logarithmically transformed. That provides that the x-ray images are processed in the state that is later ultimately intended for the display, which may be provided for a brightness compensation.

The correction algorithm provided by the provision method may in practice be used for correction of x-ray images recorded with a filter facility. Accordingly, the present embodiments also relate to a computer-implemented method for correction of an x-ray image that was recorded with an x-ray source emitting an x-ray radiation field, a filter facility spatially modulating the x-ray radiation dose (e.g., an ROI filter), and an x-ray detector, using a correction algorithm provided with a method of the present embodiments. The correction method includes determining a mask using the correction algorithm from at least the first input data assigned to the x-ray image to be corrected, and using the mask for correction of the x-ray image to be corrected.

In the event of the correction algorithm, as well as the trained first processing function, also including the trained second processing function, the first input data and the second input data are jointly seen as overall input data of the correction algorithm. Initially, the first input data (e.g., the first and second physical parameters) is used in order to determine the mask to be refined. The mask to be refined is used jointly with an x-ray image to be corrected of the second input data in order to determine the refined mask and use the refined mask for correction of the x-ray image to be corrected. The remarks relating to the provision method of the present embodiments may be transferred by analogy to the correction method of the present embodiment, with which the advantages already stated may likewise be obtained.

In one embodiment, a denoising method may additionally be applied to the corrected x-ray image. That provides that a further improvement of the corrected x-ray image with respect to its noise may be made, which also allows a reduction of the x-ray dose, since in a denoised corrected x-ray image, structures that previously may have been subject to noise are easier to recognize. Denoising methods basically known in the prior art may be employed in such cases.

The present embodiments also relate to a system for provision of a correction algorithm for an x-ray image that was recorded with an x-ray source emitting an x-ray radiation field, a filter facility spatially modulating the x-ray radiation dose (e.g., an ROI filter), and an x-ray detector. The correction algorithm includes a trained first processing function that, from first input data, which includes at least one first physical parameter describing the x-ray radiation field and/or the measurement and at least one second physical parameter describing the spatial modulation of the filter facility, determines first output data that includes a mask for brightness compensation relating to the spatial modulation of the filter facility in the x-ray image. The provision system includes a first training interface for provision of first training data including first training datasets each with a mask. Each first training dataset is assigned the first and second physical parameters of the first input data assigned for determining the mask. The provision system also includes a first training unit for training of an autoencoder for masks. The autoencoder has an encoder for determining a latent space representation of the mask and a decoder for determining a comparison mask from the latent space representation, using the first training data. The provision system includes a rule determination unit for determining an assignment rule between the physical parameters of the first input data that are assigned to the first training datasets, and the latent space representations of the masks of the respective first training dataset. The provision system includes a second training interface for provision of the trained first processing function as a combination of the assignment rule and the trained decoder.

In other words, the provision system is embodied for carrying out the provision method of the present embodiments. For this, the provision system may use at least one processor and/or at least one memory device. The corresponding functional units described may be realized by hardware and/or software.

In one embodiment of the provision system, the correction algorithm further has a trained second processing function downstream of the first trained processing function for refining the mask determined by the first processing function. The second processing function has a generator network that, as second input data, uses an x-ray image, for which the refined mask is to be determined, and a mask to be refined determined using the trained first processing function for the physical parameters of the first input data of the x-ray image of the second input data. The provision system may further have a second training interface for acceptance of x-ray images of an object (e.g., of a patient) recorded with and without filter facility, with assigned physical parameters of the first input data. The provision system may further have a second training unit for training of a generative adversarial network formed from the generator network and a discriminator network. The discriminator network is for discriminating between true x-ray images recorded without filter facility and corrected x-ray images obtained using the refined mask obtained as second output data. The second training unit is embodied for adapting the generator network and the discriminator network using an output of the discriminator network by comparing a corrected x-ray image of a second training dataset with the x-ray image of the second training dataset recorded without filter facility. The provision system may further have a fourth training interface for provision of the second correction algorithm, which includes a combination of the trained first processing function and the trained second processing function.

A system of the present embodiments for correction of an x-ray image that was recorded with an x-ray source emitting an x-ray radiation field, a filter facility spatially modulating the x-ray radiation dose (e.g., an ROI filter), and an x-ray detector has: A first application interface for acceptance of a correction algorithm provided by a provision system in accordance with the present embodiments; a second application interface for acceptance of the x-ray image to be corrected along with assigned first and second physical parameters; a mask determination unit for determining a mask by the correction algorithm from at least the first input data assigned to the x-ray image to be corrected; a correction unit for using the mask for correction of the x-ray image to be corrected; and a third application interface for provision of the corrected x-ray image.

What has been stated previously also continues to apply in relation to the correction system, where the correction system is embodied, for example, for carrying out a correction method of the present embodiments. The correction system may also have at least one processor and at least one memory device. Once again, hardware and/or software may be employed for the functional units.

The present embodiments also relate to an x-ray facility having an x-ray source, an x-ray detector, a filter facility spatially modulating the x-ray radiation dose, and a control facility. The control facility has a correction system in accordance with the present embodiments. That provides that a correction of the x-ray image by brightness compensation may be undertaken directly at the x-ray facility recording the x-ray images, which, for example, may be provided during image monitoring of medical interventions (e.g., minimally invasive interventions). For this, the x-ray facility, for example, may also have a display facility, on which the corrected x-ray image is displayed. The previous statements continue to apply for the x-ray facility. Embodiments in which the x-ray facility, in addition to the correction system, may also have a provision system in accordance with the present embodiments as part of the control facility may also be provided.

The x-ray facility of the present embodiments may be embodied, for example, as an x-ray facility with a C-arm, on which the x-ray source and the x-ray detector are arranged opposite one another. Such C-arm x-ray facilities are frequently used in medical interventions for fluoroscopy, so that such C-arm x-ray facilities may also be referred to as interventional C-arm x-ray facilities.

A computer program of the present embodiments is able to be loaded directly into a memory device of a computing facility (e.g., a computing facility of a provision system and/or of a correction system) and/or a control facility of an x-ray facility and has program means for carrying out the acts of the correction method and/or provision method described herein when the computer program is executed on the computing facility or the control facility. The computer program may be stored on an electronically readable data medium in accordance with the present embodiments, which thus includes control information that includes at least one computer program of the present embodiments and is embodied in such a way that, when the data medium is used in a computing facility, the medium carries out the acts of a provision method and/or correction method in accordance with the present embodiments. The data medium may, for example, involve a non-volatile data medium (e.g., a non-transitory computer-readable storage medium such as a CD-ROM).

BRIEF DESCRIPTION OF THE DRAWINGS

Further advantages and details of the present invention emerge from the exemplary embodiments described below and also with the aid of the drawings. In the drawings.

DETAILED DESCRIPTION

Figure 1:
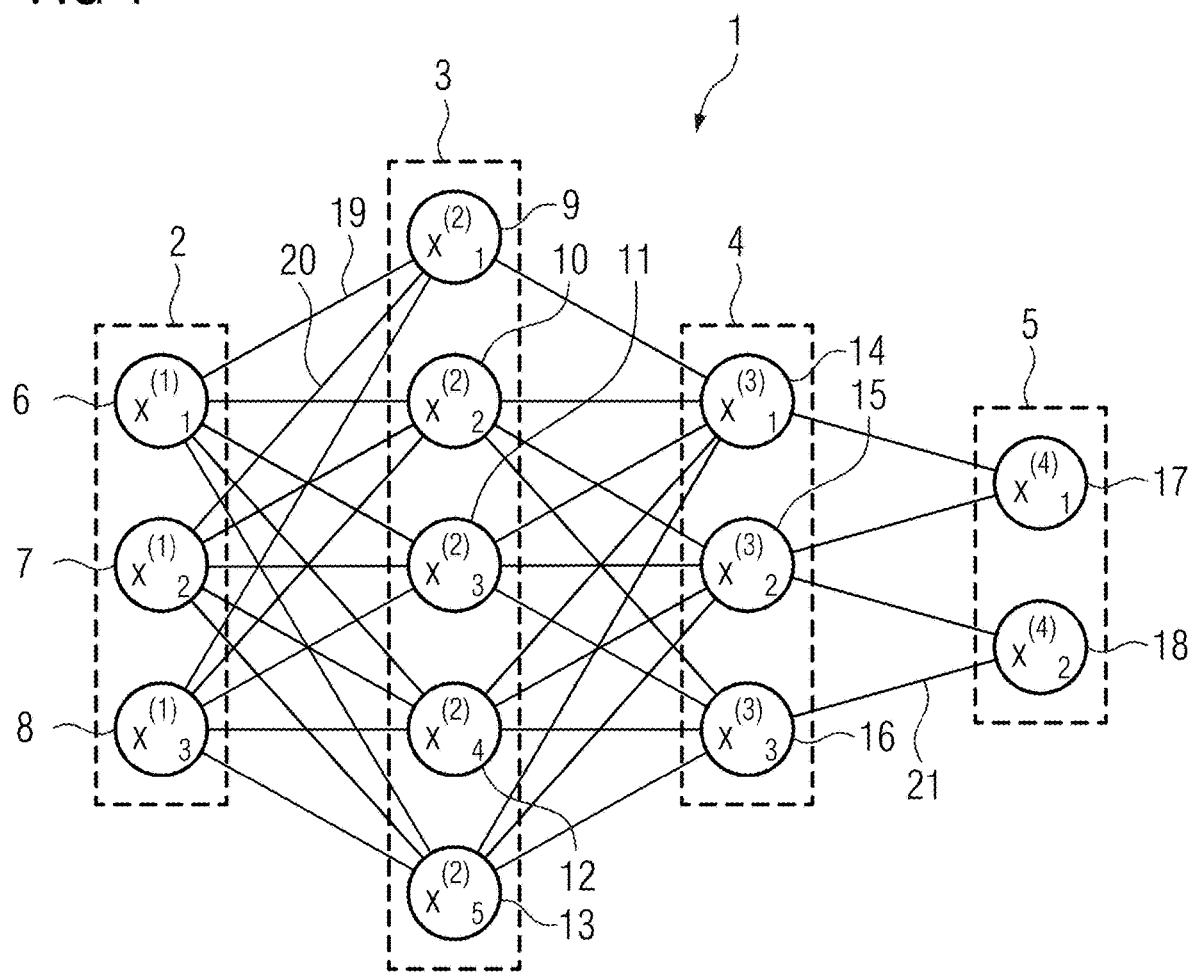
FIG. 1 shows an exemplary embodiment of a neural network.

FIG. 1 shows an exemplary embodiment of an artificial intelligence neural network 1. Other expressions for such a network are "artificial neural network," "neural network," "artificial neural net," or "neural net".

The artificial neural network 1 includes nodes 6 to 18 and edges 19 to 21, where each edge 19 to 21 is a directed connection from a first node 6 to 18 to a second node 6 to 18. In general, the first node 6 to 18 and the second node 6 to 18 are different nodes 6 to 18. In one embodiment, the first node 6 to 18 and the second node 6 to 18 may be identical. For example, in FIG. 1, the edge 19 is a directed connection from the node 6 to the node 9, and the edge 21 is a directed connection from the node 16 to the node 18. An edge 19 to 21 from a first node 6 to 18 to a second node 6 to 18 is referred to as the ingoing edge for the second node 6 to 18 and as the outgoing edge for the first node 6 to 18.

In this exemplary embodiment, the nodes 6 to 18 of the artificial intelligence neural network 1 may be arranged in layers 2 to 5, where the layers 2 to 5 may have an intrinsic order that is introduced by the edges 19 to 21 between the nodes 6 to 18. For example, edges 19 to 21 may only be provided between neighboring layers of nodes 6 to 18. In the exemplary embodiment shown, there exists an input layer 110 that only has the nodes 6, 7, 8, without an ingoing edge in each case. The output layer 5 includes only the nodes 17, 18, without outgoing edges in each case, where further hidden layers 3 and 4 lie between the input layer 2 and the output layer 5. In the general case, any number of hidden layers 3, 4 may be chosen. The number of the nodes 6, 7, 8 of the input layer 2 may correspond to the number of input values in the neural network 1, and the number of nodes 17, 18 in the output layer 5 may correspond to the number of output values of the neural network 1.

For example, a number (e.g., a real number) may be assigned to the nodes 6 to 18 of the neural network 1. In this case, $x^{(n)}_i$ refers to the value of the ith node 6 to 18 of the nth layer 2 to 5. The values of the nodes 6, 7, 8 of the input layer 2 are equivalent to the input value of the neural network 1, while the values of the nodes 17, 18 or the output layer 5 are equivalent to the output values of the neural network 1. Further, edge 19, 20, 21 may be assigned a weight in the form of a real number. For example, the weight is a real number in the interval [−1, 1] or in the interval [0, 1,]. In this case, $w^{(m,n)}_{i,j}$ refers to the weight of the edge between the ith node 6 to 18 of the mth layer 2 to 5 and the jth node 6 to 18 of the nth layer 2 to 5. The abbreviation $w^{(n)}_{i,j}$ is further defined for the weight $w^{(n,n+1)}_{i,j}$.

In order to calculate output values of the neural network 1, the input values are propagated through the neural network 1. For example, the values of the nodes 6 to 18 of the (n+1)th layer 2 to 5 may be calculated based on the values of the nodes 6 to 18 of the nth layer 2 to 5 by $$x_j^{(n+1)} = f(\Sigma_i x_i^{(n)} \cdot w_{i,j}^{(n)}).$$

In this equation, f is a transfer function that may also be referred to as an activation function. Known transfer functions are step functions, Sigmoid functions (e.g., the logistical function, the generalized logistical function, the tangens hyperbolicus, the arcustangens, the error function, the smooth step function) or rectifier functions. The transfer function is essentially used for standardization purposes.

For example, the values are propagated layer-by-layer through the neural network 1, where values of the input layer 2 are given by the input data of the neural network 1. Values of the first hidden layer 3 may be calculated based on the values of the input layer 2 of the neural network 1, values of the second hidden layer 4 may be calculated based on the values in the first hidden layer 3, etc.

In order to be able to define the values $w_{i,j}^{(n)}$ for the edges 19 to 21, the neural network 1 is to be trained using training data. For example, training data includes training input data and training output data, which are referred to below as $t_i$. For a training step, the neural network 1 is applied to the training input data in order to determine calculated output data. For example, the training output data and the calculated output data include a number of values, where the number is determined as the number of the nodes 17, 18 of the output layer 5.

For example, a comparison between the calculated output data and the training output data is used in order to recursively fit the weights within the neural network 1 (e.g., back propagation algorithm). For example, the weights may be changed in accordance with $$w'^{(n)}_{i,j} = w^{(n)}_{i,j} - \gamma \cdot \delta_j^{(n)} \cdot x_i^{(n)}$$

where γ is a learning rate, and the numbers $\delta_j^{(n)}$ may be calculated recursively as $$\delta_j^{(n)} = (\Sigma_k \delta_k^{(n+1)} \cdot w_{j,k}^{(n+1)}) \cdot f'(\Sigma_i x_i^{(n)} \cdot w_{i,j}^{(n)})$$

based on $\delta_j^{(n+1)}$, when the (n+1)th layer is not the output layer 5, and $$\delta_j^{(n)} = (x_k^{(n+1)} - t_j^{(n+1)}) \cdot f'(\Sigma_i x_i^{(n)} \cdot w_{i,j}^{(n)})$$

the (n+1)th layer is the output layer 5, where f' is the first derivation of the activation function, and yj(n+1) is the comparison training value for the jth node 17, 18 of the output layer 5.

Figure 2:
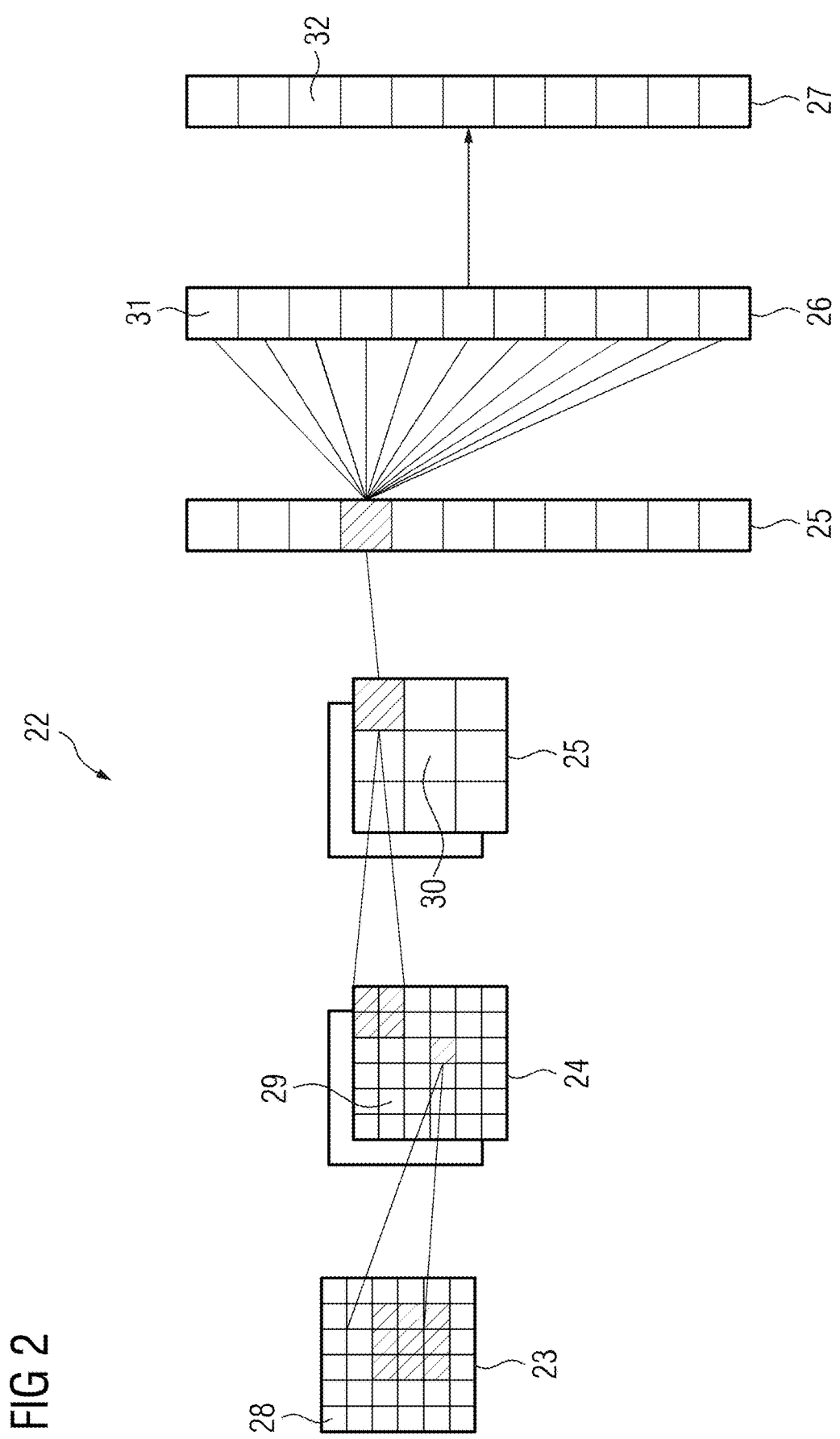
FIG. 2 shows an exemplary embodiment of a convolutional neural network (CNN)

Also given below with respect to FIG. 2 is an example for a convolutional neural network (CNN). In this example, the expression "layer" in the figure is employed in a slightly different way than for classical neural networks. For a classical neural network, the expression "layer" only refers to the set of nodes that forms a layer, and thus, to a specific generation of nodes. For a convolutional neural network, the expression "layer" is often used as an object that actively changes data (e.g., as a set of nodes of the same generation and either the set of ingoing or outgoing edges).

FIG. 2 shows an exemplary embodiment of a convolutional neural network 22. In the exemplary embodiment shown, the convolutional neural network 22 includes an input layer 23, a convolutional layer 24, a pooling layer 25, a fully connected layer 26, and an output layer 27. In alternate embodiments, the convolutional neural network 22 may contain a number of convolutional layers 24, a number of pooling layers 25, and a number of fully connected layers 26, just like other types of layers. A given sequence of the layers may be selected, where usually fully connected layers 26 form the last layers before the output layer 27.

For example, within a convolutional neural network 22, the nodes 28 to 32 of one of the layers 23 to 27 may be arranged in a d-dimensional matrix or as a d-dimensional image. For example, in the two-dimensional case, the value of a node 28 to 32 may be referred to with the indices i, j in the nth layer 23 to 27 as $x^{(n)}[i,j]$. The arrangement of the nodes 28 to 31 of a layer 23 to 27 does not have any effect as such on the calculations within the convolutional neural network 22 as such, since these effects are exclusively produced by the structure and the weights of the edges.

A convolutional layer 24 is, for example, characterized in that the structure and the weights of the ingoing edges form a convolution operation based on a specific number of kernels. For example, the structure and the weights of the ingoing edges may be selected so that the values $x_k^{(n)}$ of the nodes 29 of the convolutional layer 24 are determined as a convolution $x_k^{(n)} = K_k * x^{(n-1)}$ based on the values $x^{(n-1)}$ of the node 28 of the preceding layer 23, where the convolution * in the two-dimensional case may be defined as $$x_k^{(n)}[i,j] = (K_k * x^{(n-1)})[i,j] = \Sigma_{i'} \Sigma_{j'} K_k[i',j'] \cdot x^{(n-1)}[i-i',j-j'].$$

In this equation, the kth kernel $K_k$ is a d-dimensional matrix (e.g., a two-dimensional matrix) that may be small by comparison with the number of the nodes 28 to 32 (e.g., a 3×3 matrix or a 5×5 matrix). For example, this implies that weights of the ingoing edges are not independent, but are selected so that the weights create the convolution equation above. In the example for a kernel that forms a 3×3 matrix, there exist only nine independent weights (e.g., where each entry of the kernel matrix corresponds to an independent weight), regardless of the number of the nodes 28 to 32 in the corresponding layers 23 to 27. For example, for a convolutional layer 24, the number of the nodes 29 in the convolutional layer 24 is equivalent to the number of the nodes 28 in the preceding layer 23 multiplied by the number of the convolution kernels.

When the nodes 28 of the preceding layer 23 are arranged as a d-dimensional matrix, the use of the plurality of kernels may be understood as the insertion of a further dimension, which is also referred to as a depth dimension, so that the nodes 29 of the convolutional layer 24 are arranged as a (d+1)-dimensional matrix. When the nodes 28 of the preceding layer 23 are already arranged as a (d+1)-dimensional matrix with a depth dimension, the use of a plurality of convolution kernels may be understood as an expansion along the depth dimension, so that the nodes 29 of the convolutional layer 24 are equally arranged as a (d+1)-dimensional matrix. The size of the (d+1)-dimensional matrix in the depth dimension is greater by the factor formed by the number of the kernels than in the preceding layer 23.

The advantage of using convolution kernels 24 is that the spatially local correlation of the input data may be utilized by a local connection pattern between nodes of neighboring layers being created (e.g., in that each node only has connections to a small area of the node of the preceding layer).

In the exemplary embodiment shown, the input layer 23 includes thirty-six nodes 28 that are arranged as a two-dimensional 6×6 matrix. The convolutional layer 24 includes seventy-two nodes 29 that are arranged as two two-dimensional 6×6-matrices, where each of the two matrices is the result of a convolution of the values of the input layer 23 with a convolution kernel. In the same way, the nodes 29 of the convolutional layer 24 may be understood as being arranged as a three-dimensional 6×6×2 matrix, where the last-mentioned dimension is the depth dimension.

A pooling layer 25 is characterized in that the structure and the weights of the ingoing edges as well as the activation function of its nodes 30 define a pooling operation based on a non-linear pooling function f. For example, in the two-dimensional case, the values $x^{(n)}$ of the nodes 30 of the pooling layer 25 may be calculated, based on the values $x^{(n+1)}$ of the nodes 29 of the preceding layer 24, as $$x^{(n)}[i,j] = f(x^{(n-1)}[id_1, jd_2], \ldots, x^{(n-1)}[id_1 + d_1 - 1, jd_2 + d_2 - 1]).$$

In other words, the number of nodes 29, 30 may be reduced by the use of a pooling layer 25, in that a number of $d_1 \times d_2$ of neighboring nodes 29 in the preceding layer 24 is replaced by a single node 30 that is calculated as a function of the values of the the number of neighboring nodes 29. For example, the pooling function f may be a maximum function, an averaging or the L2 norm. For example, for a pooling layer 25, the weights of the ingoing edges may be defined and not modified by training.

The advantage of using a pooling layer 25 is that the number of nodes 29, 30 and the number of parameters is reduced. This leads to a reduction in the amount of calculations necessary within the convolutional neural network 22 and thus to a control of the overfitting.

In the exemplary embodiment shown, the pooling layer 25 involves a max pooling layer, in which four neighboring nodes are replaced by just one single node, the value of which is formed by the maximum of the values of the four neighboring nodes. The max pooling is applied to each d-dimensional matrix of the preceding layer; in this exemplary embodiment, the max pooling is applied to each of the two two-dimensional matrices, so that the number of nodes is reduced from seventy-two to eighteen.

A fully connected layer 26 is characterized by a plurality (e.g., all) edges being present between the nodes 30 of the preceding layer 25 and the nodes 31 of the fully connected layer 26, where the weight of each of the edges may be fitted individually. In this exemplary embodiment, the nodes 30 of the preceding layer 25 and the fully connected layer 26 are both shown as two-dimensional matrices and also as non-contiguous nodes (shown as a row of nodes, where the number of the nodes has been reduced so that the nodes may be shown more easily). In this exemplary embodiment, the number of nodes 31 in the fully connected layer 26 is equal to the number of the nodes 30 in the preceding layer 25. In alternate forms of embodiment, the number of the nodes 30, 31 may be different.

Further, in this exemplary embodiment, the values of the nodes 32 of the output layer 27 are determined by the softmax function being applied to the values of the nodes 31 of the preceding layer 26. Through application of the softmax function, the sum of the values of all nodes 32 of the output layer 27 is one, and all values of all nodes 32 of the output layer are a real number between 0 and 1. When the convolutional neural network 22 is used for classification of input data, the values of the output layer 27, for example, may be interpreted as the probability of the input data falling into one of the different classes.

A convolutional neural network 22 may likewise have a ReLU layer, where ReLU is an acronym for "rectified linear units". For example, the number of the nodes and the structure of the nodes within a ReLU layer is equivalent to the number of the nodes and the structures of the nodes of the preceding layer. The value of each node in the ReLU layer may be calculated, for example, by application of a rectifier function to the value of the corresponding node of the preceding layer. Examples of rectifier functions are f(x)=max(0,x), the tangens hyperbolicus, or the Sigmoid function.

Convolutional neural networks 22 may be trained, for example, based on the back propagation algorithm. In order to avoid an overfitting, methods of regularization may be employed (e.g., dropout of individual nodes 28 to 32), stochastic pooling, use of artificial intelligence data, weight decomposition based on the L1 or the L2 standard, or maximum standard restrictions.

Figure 3:
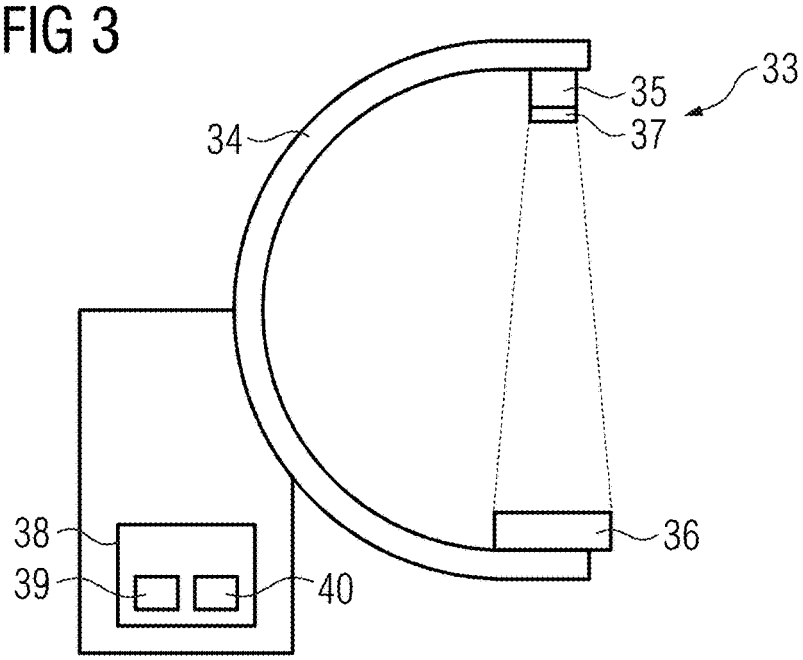
FIG. 3 shows a basic sketch of an embodiment of an x-ray facility.

FIG. 3 shows a basic sketch of one embodiment of an x-ray facility 33. The x-ray facility 33 has a C-arm 34, on which an x-ray source 35 (e.g., an x-ray tube) and an x-ray detector 36 are arranged opposite one another. The x-ray facility 33 further includes a filter facility 37 (e.g., an ROI filter) that may be used, for example, for x-ray monitoring of medical interventions (e.g., minimally invasive interventions) for reducing the x-ray radiation dose for the patient and the medical personnel. The operation of the x-ray facility 33 is controlled by a control facility 38 that is embodied as a correction system 39 for correction of x-ray images for balancing brightness recorded with the filter facility 37, since the filter facility 37 is embodied for spatial modulation of the x-ray radiation dose. Optionally, the control facility 38 may also include a provision system 40. While the correction system 39 is embodied for carrying out a correction method of one or more of the present embodiments, the provision system 40 is embodied for carrying out a provision method of one or more of the present embodiments, which will be explained in greater detail below.

Figure 4:
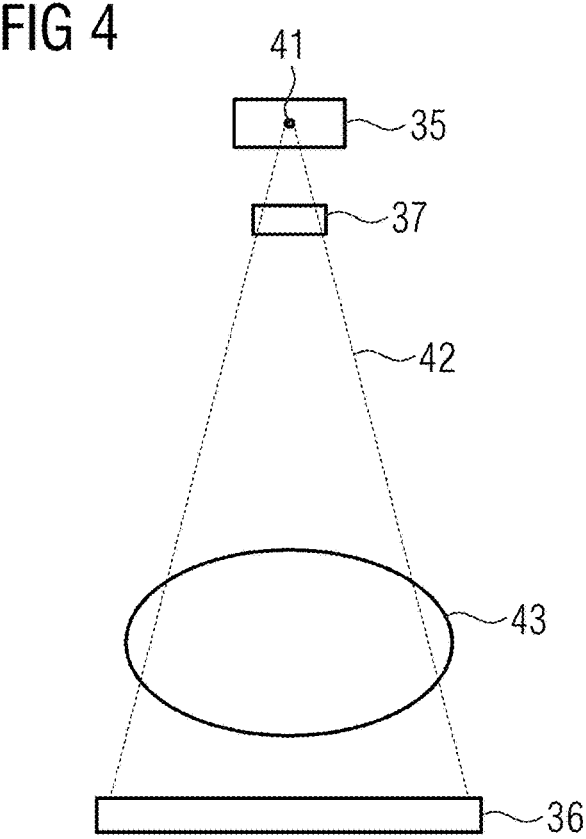
FIG. 4 shows a recording geometry produced during the recording of a patient.

FIG. 4 shows in greater detail the recording geometry when the filter facility 37 is used. The x-ray source 35, starting from a focus point 41, creates an x-ray radiation field 42 in order to record a recording region of a patient 43 only shown schematically here. This may also result in effects lying outside the filter facility 37, which relate to the mapping of the filter facility 37 on the x-ray detector 36; in accordance with the present embodiments, these are likewise to be taken into account in a brightness compensation (e.g., the determination of a brightness correction mask). Thus, with an x-ray tube, for example, this may result in a "jittering" of the focus point 41, which, due to the filter facility 37 being arranged close to the focus point 41 (e.g., at a distance of 5 cm) may be mapped in a relevant way as a "wobbling" of specific regions. It may further also be relevant that the focus point 41 is mostly not completely punctiform, but has a specific geometry. Also, the patient 43, by beam hardening, scattered radiation, and the like, may have an influence on the mapping of the filter facility 37 at the x-ray detector 36, where the setting of the x-ray detector 36 itself is to be further mentioned. For determining a correct brightness correction mask to be used for brightness compensation, not only knowledge about the filter facility 37 and its state during imaging is relevant, but also about other aspects (e.g., system settings for dynamics of the situation and influences of the patient 43).

Figure 5:
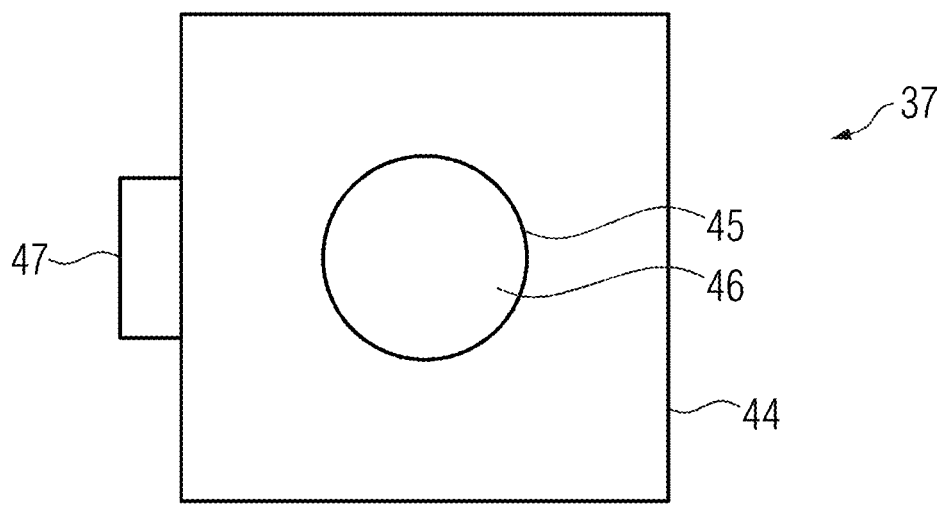
FIG. 5 shows a filter facility embodied as an ROI filter.

FIG. 5 shows an exemplary embodiment of the filter facility 37 as an ROI filter in more detail. The filter facility 37 consists of a filter material 44 (e.g., tungsten) that has a central passage opening 46 that defines an ROI 45, in which the standard dose of x-ray radiation is still present, while outside the ROI 45, a strong attenuation of the x-ray radiation through the filter material 44 (e.g., a thin tungsten layer) is present. The filter facility 37 may further have an actuator system 47, by which the size and/or position of the ROI 45 may be able to be changed (e.g., by exchanging various filter plates available, movement of the filter material 44, or the like). The actuator system 47 may be actuated, for example, as a function of user inputs, for tracking a medical instrument (e.g., a catheter), and/or as a function of eye tracking data.

Figure 6:
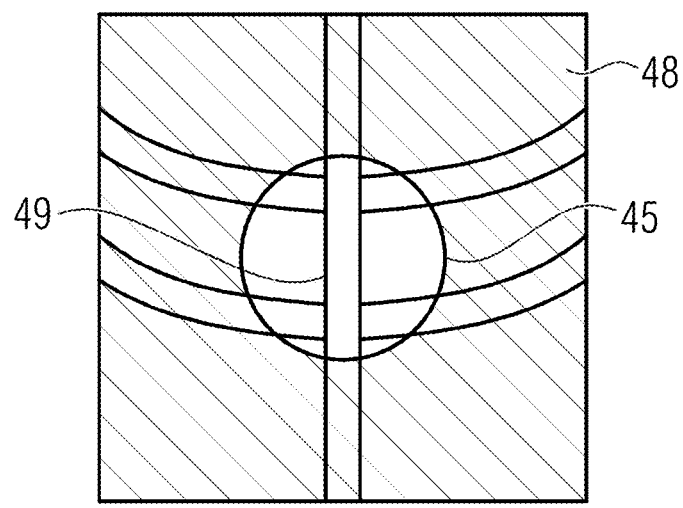
FIG. 6 shows a schematic diagram of an x-ray image to be corrected recorded using the filter facility in accordance with FIG. 5.

FIG. 6 shows a schematic of an x-ray image 48 to be corrected that was recorded using the filter facility 37 of FIG. 5. The ROI 45 is mapped clearly visibly in the x-ray image 48, since there, the anatomy 49 of the patient 43 appears far brighter than in the outer regions surrounding the ROI 45, as is indicated by the cross hatching. As has already been explained, a smooth transition is mostly produced in this case, where, however, the geometrical form of the opening 46, due to dynamic effects, such as the jittering of the focus point 41, is not necessarily reproduced in the exact correct form.

Figure 7:
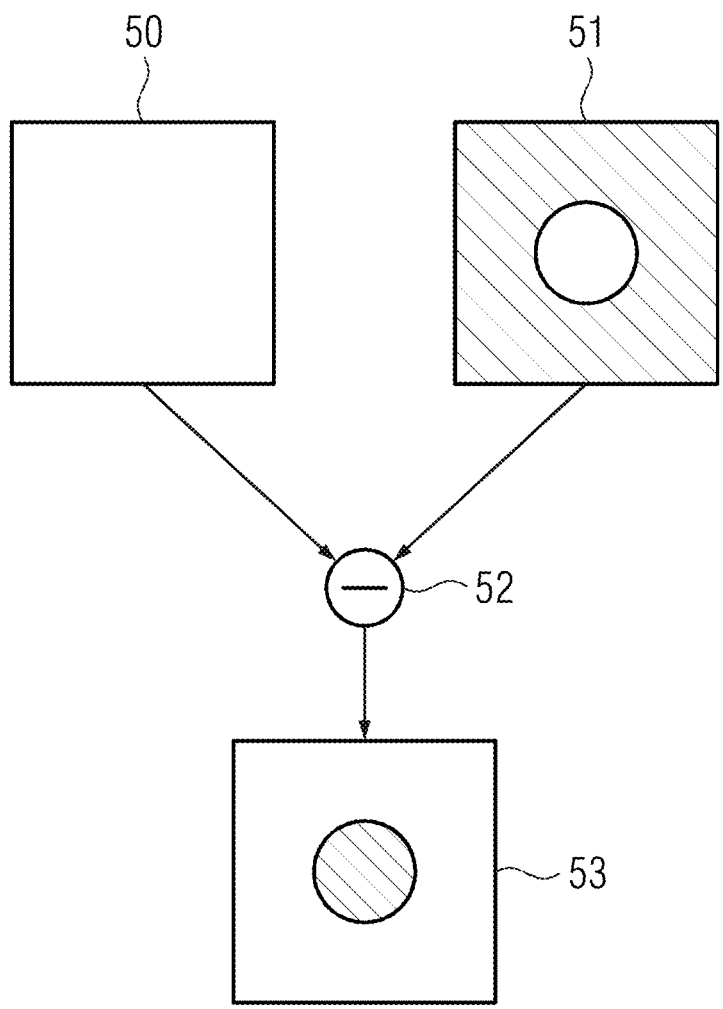
FIG. 7 shows a diagram for determining a mask for correction of an x-ray image to be corrected.

FIG. 7 shows an option for how a mask may be determined, such as at least with regard to system settings and their effects (e.g., in a calibration measurement). In this case, two x-ray images 50, 51 without a patient 43 with specific, fixed system settings, described by first and second physical parameters, may be recorded. The x-ray image 50 is a flat-field x-ray image without the filter facility 37 as object, while the x-ray image 51 is a flat-field x-ray image for which the filter facility 37 has been used. If the x-ray image 51 is now subtracted from the x-ray image 50 (cf., act 52), a mask 53 is produced. In this case, the x-ray images 50, 51 are logarithmically transformed, as usual, before determination of the mask 53. The mask 53 may be employed for additive correction of an x-ray image 48 to be corrected, when exactly the same system settings are present, where, however, the described dynamic effects as well as the effects by the patient 43 may then not be taken into account. This, however, makes possible the procedure in accordance with the exemplary embodiments described here, with which extremely expensive calibration measurements for all conceivable system settings are avoided.

Figure 8:
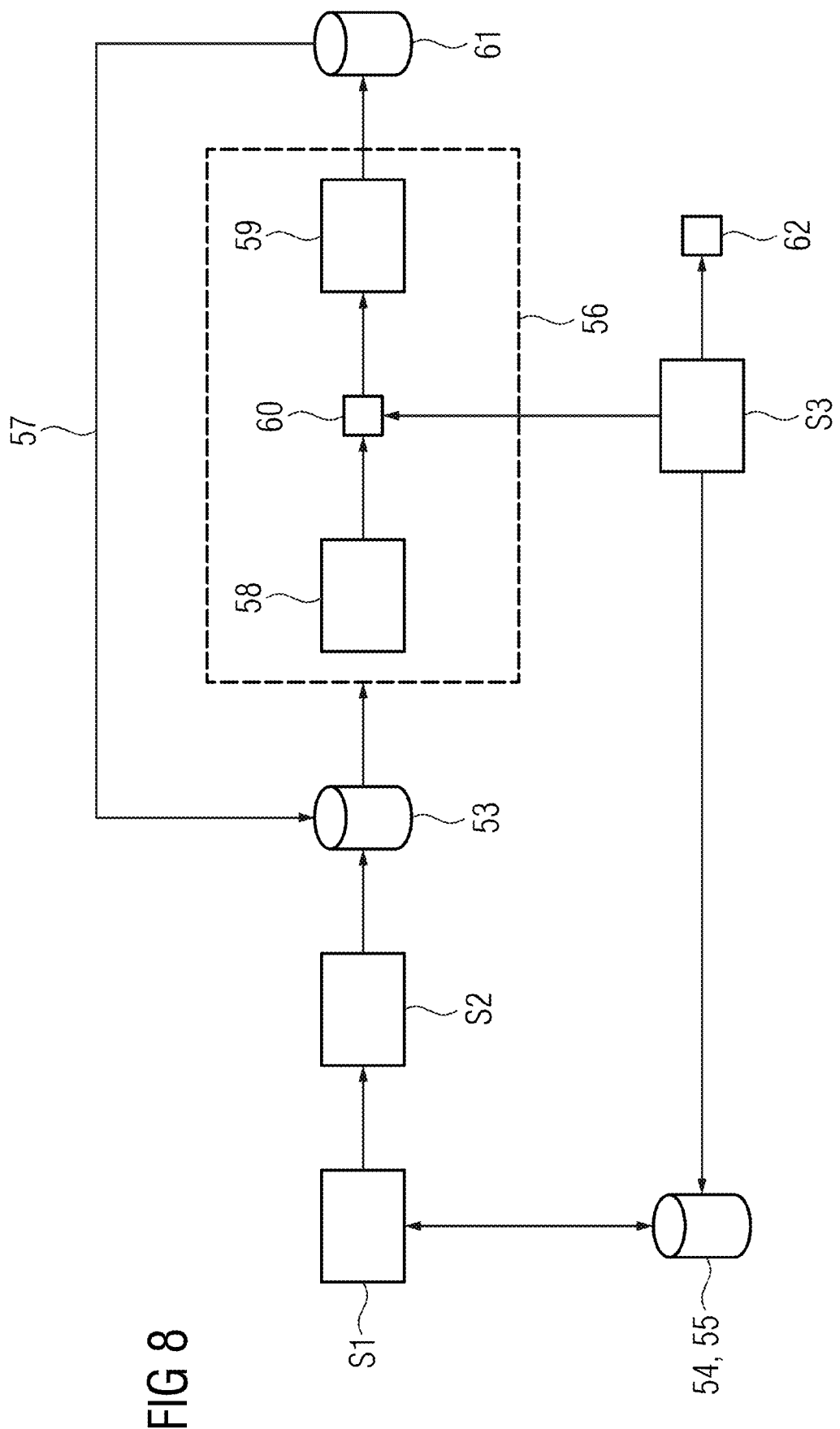
FIG. 8 shows a flow diagram of a first stage of one embodiment of a provision method.

A provision method in accordance with the present embodiments is now described with reference to FIGS. 8 and 9, where FIG. 8 relates to the training of the first processing function, thus to the first stage, and FIG. 9 relates to the training of the second stage, thus to the second processing function. By combination of the trained first processing function and the trained second processing function, a highly accurate mask for correction of x-ray images 48, encompassing many effects for use in a correction algorithm of the present embodiments, may be provided.

The first processing algorithm relates to the characteristics of the measurement itself (e.g., the technical settings or system settings, such as creation of the x-ray radiation, geometry, detector operation, characteristics, or settings of the filter facility). In order to train the first processing algorithm, in acts S1 and S2, using the method described for FIG. 7, first training data is recorded, where each training dataset includes a mask 53 and also the first and second physical parameters 54, 55 used in the recording of the mask 53, to be used as first input data.

The first and second physical parameters describe system settings of the x-ray facility 33 used. For example, first physical parameters are concerned with the x-ray radiation field, its creation, and the measurement, also including the recording geometry and the operation of the x-ray detector 36, and second physical parameters 55 are explicitly concerned with the characteristics of the filter facility 37. For example, the second physical parameters 55 may relate to the filter material, the filter material thickness, as well as the size and the location of the ROI 45, if necessary also temporarily by a time parameter. First physical parameters 54 may, for example, relate to settings of the x-ray source (e.g., tube current, tube voltage, and pulse length), focus point settings (e.g., focus point sizes and angles), detector settings (e.g., zoom, orientation, and frame rate), as well as the recording geometry (e.g., SID, SOD and OID, where the filter facility 37 counts as the object). In this case, the physical parameters 54, 55 to be used in the calibration are, where possible, chosen so that the physical parameters 54, 55 cover the setting space relevant for the actual recordings.

With the settings of the first and second physical parameters, in act S1, x-ray images 50 and 51 are recorded, as described for FIG. 7. In act S2, respective masks 53 are determined from the x-ray images 50 and 51, as described. With the assignment of the first and second physical parameters 54, 55 to these first masks, the first training data is determined, so that an autoencoder 56 for the masks 53, as is basically known, may be trained, which is indicated by the arrow 57. The autoencoder 56 includes, as is basically known, at least one CNN, where an encoder 58 and a decoder 59 are formed. A latent space representation 60 with just a few latent space parameters is determined by the encoder 58, which should be sufficient for the mask 53 to be reproduced as exactly as possible by the decoder 59. In other words, the decoder 59, during the training in accordance with arrow 57, delivers comparison masks 61 that may be compared with the respective input mask 53 of the respective training data, where the deviation is minimized.

A relationship exists between the latent space representation 60 and the first and second physical parameters. Sets of first and second physical parameters, between which there are only few or small changes, deliver similar latent space representations 60 in this case. If a physical parameter 54, 55 changes the recording, latent space parameters also having a relationship with this physical parameter, which indeed map relevant characteristics, change. If, for example, the distance changes between the x-ray source 35 and the x-ray detector 36 (SID), where the distance from the x-ray source 35 to the filter facility 37 (SOD) remains constant, however, the opening 46 is mapped larger, so that changes in latent space parameters relating to this characteristic occur. The fact that a relationship exists at least with a part of the first and second physical parameters 54, 55 is utilized in act S3 in order to determine an assignment rule 62 from latent space representations 60 (e.g., in specific terms, latent space parameters) to any given sets of first and second physical parameters 54, 55, which may contain functional relationships between the first and second physical parameters 54, 55 and the latent space parameters of the latent space representation 60. The functional relationships may be parameterized by fitting and/or interpolation and/or extrapolation. Accordingly, the assignment rule 62 for any given system settings (e.g., any given first and second physical parameters 54, 55) allows the associated latent space representation 60 to be determined, so that using the trained decoder 59, a rough estimation of a mask used in training of the second processing function accordance with FIG. 9 may be determined. Accordingly, for the first stage, as output of the trained first processing function 63 (cf., FIG. 9), a combination of the assignment rule 62 and the decoder 59 may be provided. This provides that the trained first processing function uses as input data the first and second physical parameters 54, 55 in order to output as first output data a mask 64 still to be refined by the second stage.

Figure 9:
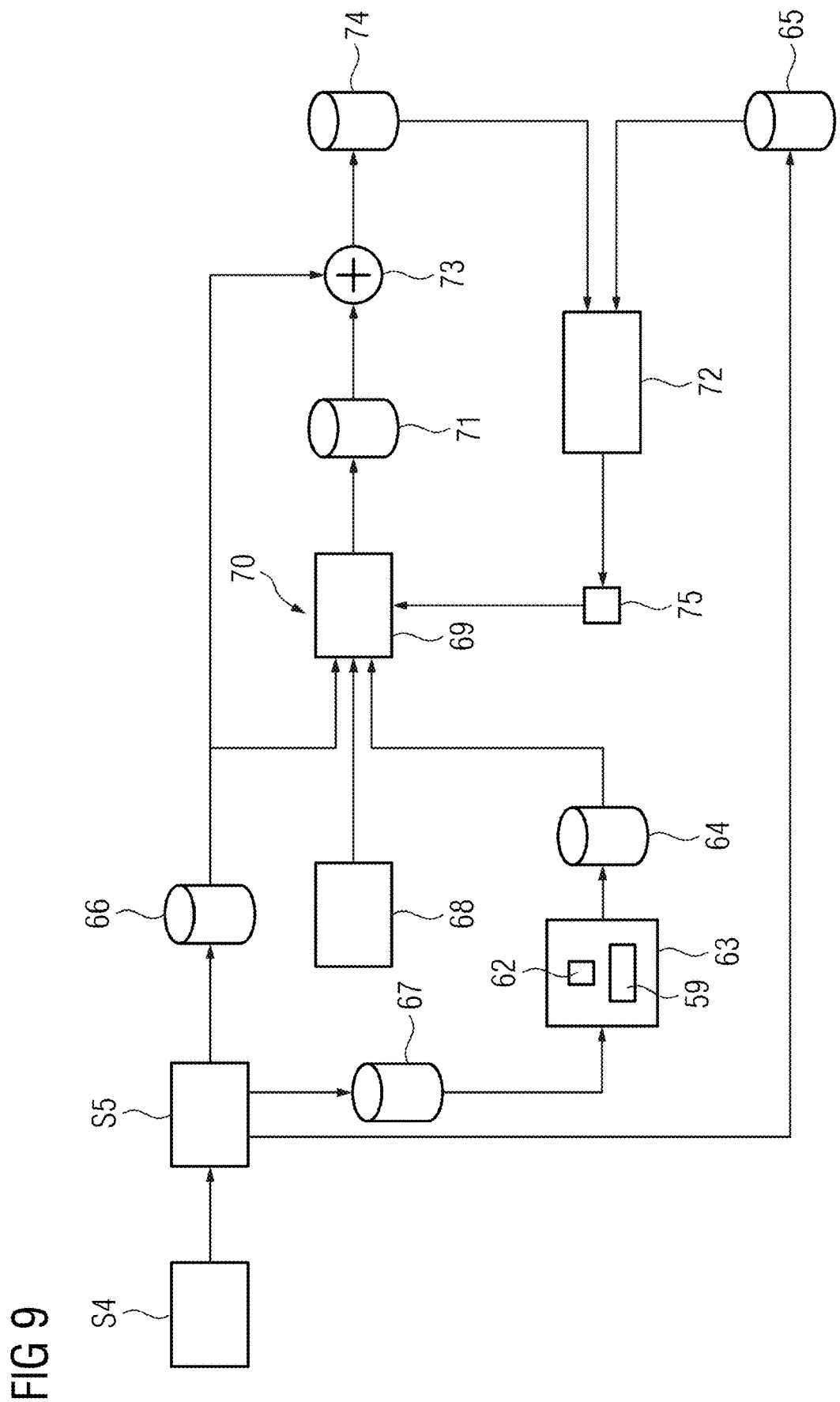
FIG. 9 shows a flow diagram of a second stage of one embodiment of a provision method.

In accordance with FIG. 9, the second processing function is trained and provided. In order to now first determine the second training data, in act S4 taking place over a longer period of time, pairs of images of x-ray images 65 of different patients without filter facility 37 and x-ray images of the same patient in each case using the same physical parameters 54, 55 with filter facility 13 are recorded and in act S5 logarithmically transformed, as is basically known. This provides that the second training data includes a pair of images consisting of one x-ray image 65 that was recorded without filter facility 13 and an x-ray image 66 that was recorded with filter facility 37, as well as the first and second physical parameters 54, 55 used for the recording, associated first input data (shown by way of summary in FIG. 9 as first input data with the reference character 67). The x-ray images 65, 66 in exemplary embodiments do not necessarily have to show the same object and/or the same point in time, but certainly may.

Due to the trained first processing function 63, it is possible, for each pair of images 65, 66, using this mask 64 to be refined, to determine a generator network 69 that forms the second processing function 70 as first output data. These, together with boundary conditions 68 still to be discussed as well as the respective x-ray images 66 to be corrected, recorded with the filter facility 37, form second input data for the second processing function 70, which as second output data 69, should deliver a refined mask 71. In order to train the second processing function 70, a generative adversarial network (GAN) is created, in that a discriminator network 72 that serves to discriminate between x-ray images 74 corrected by the refined mask 71 present by addition 73 and true x-ray images 65 is inserted. As output, the discriminator network 72 delivers an adversarial loss 75 or classification loss, which, in simple terms, expresses how unrealistic the corrected x-ray image 74 still is by comparison with the realistic x-ray image 65. This adversarial loss is to be minimized and is thus used during the training process 76 for fitting the generator network 69 as well as the discriminator network 72, as is basically known.

The result of the training process 76 is then the trained second processing function 70, which delivers refined masks 71.

The boundary conditions serve various purposes and may, for example, make sure that refined masks 71 do not deviate too much from the specification or the space of possible masks 64, that the smoothness of the mask 71 is provided and that only a specific set of arithmetical operations may be carried out in order to get from the input mask 64 to the refined mask 71. In this way, the generator network 69 (e.g., based on physical observations, such as an analysis of the space of masks 53 obtained in the acts S1 and S2) is prevented from creating unrealistic outputs, which may then irritate medical personnel if applied (e.g., by causing artifacts to arise).

The addition of the trained second processing function 70 for correction allows aspects, such as, where necessary, variable geometry and position of the ROI 45 due to the jittering of the focus point 41 at low pulse lengths, movements of the ROI 45 (e.g., due to eye tracking), effects caused by patients recorded, such as beam hardening and the like, to be taken into consideration. At the same time, the mask 64 may be adapted with respect to the general brightness stabilization.

Figure 10:
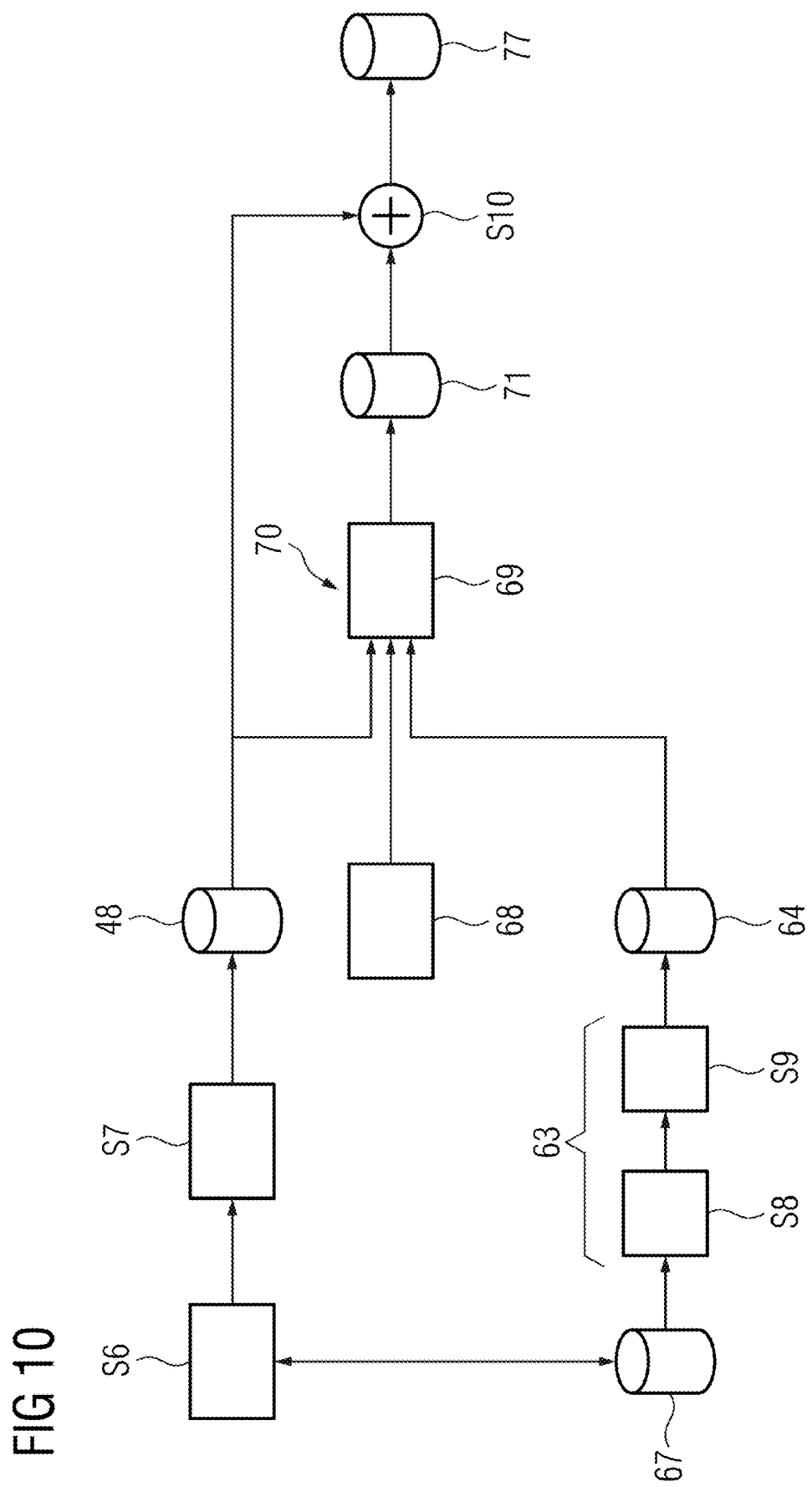
FIG. 10 shows a flow diagram of one embodiment of a correction method.

FIG. 10 shows a flow diagram of an exemplary embodiment of a correction method. According to the method, in act S6, using first and second physical parameters 54, 55 (e.g., first input data 67), an x-ray image 48 to be corrected is recorded and logarithmically transformed in act S7. The trained first processing function 63 is then used in order to determine the mask 64 to be refined, in that first, in act S8, the assignment rule 62 is used in order to determine the latent space representation 60; after this, in act S9, the trained decoder 59 is used in order to determine the mask 64 to be refined from the latent space representation 60 determined. The x-ray image 48 to be corrected, the mask 64 to be refined, and also the boundary condition 68 form the second input data for the generator network 69 provided as second trained processing function, which thus delivers the refined mask 71 as output data. In act S10, the refined mask 71, in order to achieve the brightness compensation, is corrected to the x-ray image 48 to be corrected, so that a corrected x-ray image 77 arises.

A denoising may then be applied to this corrected x-ray image 77 in order to further improve the image quality and in this way possibly to allow a further reduction of the x-ray dose.

Figure 11:
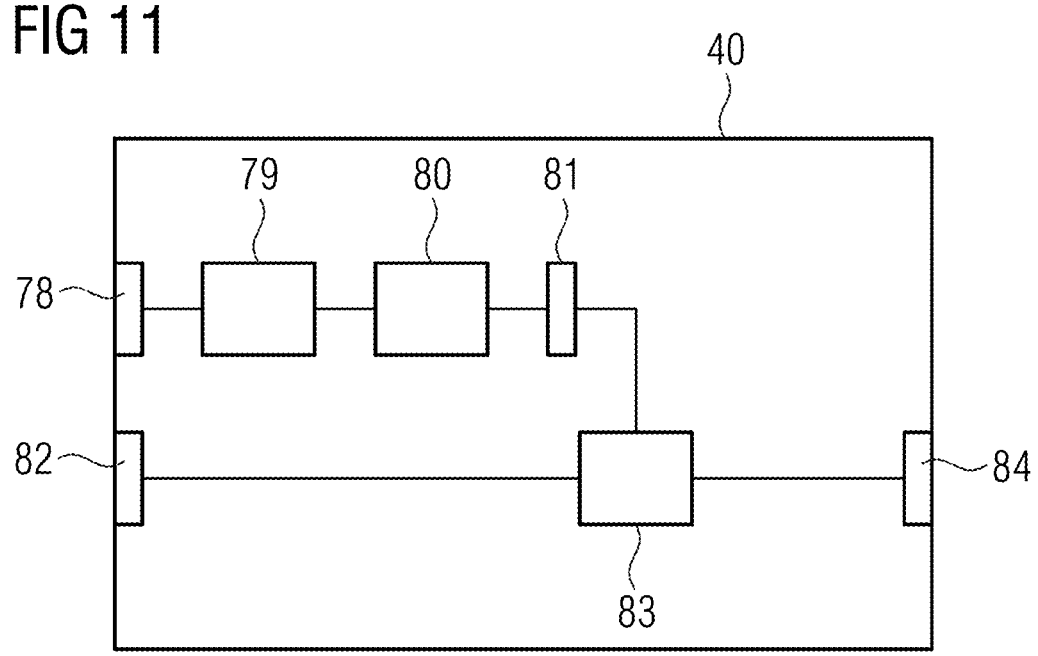
FIG. 11 shows the functional structure of a provision system in accordance with an embodiment.

FIG. 11 explains the functional layout of one embodiment of a provision system 40 that may also be referred to as a training system. The provision system 50 has a first training interface 78, via which the first training data (e.g., masks 53 with assigned physical parameters 54, 55) are accepted. In a first training unit 79, the autoencoder 56 is trained as described in accordance with FIG. 8 (cf., arrow 57). After this, in a rule determination unit 80, the assignment rule in accordance with act S3 may be determined.

A second training interface 81 in the present case involves an internal interface, via which the trained first processing function 63 may be provided as a combination of the assignment rule 62 and the trained decoder 59.

The provision system 40 now also has a third training interface 82, via which the second training data for the second stage is accepted (e.g., the x-ray images 65 and 66 as well as the first input data 67 (physical parameters 54, 55) in accordance with FIG. 9). A second training unit 83 trains the generator network 69 as the second processing function 70 using this second training data, as has been described in detail with regard to FIG. 9, in the sense of an adversarial training. The first processing function 62 has then been trained by representation learning. The correction algorithm, including the trained first processing function 62 and the trained second processing function 70 is then provided via a fourth training interface 84.

Figure 12:
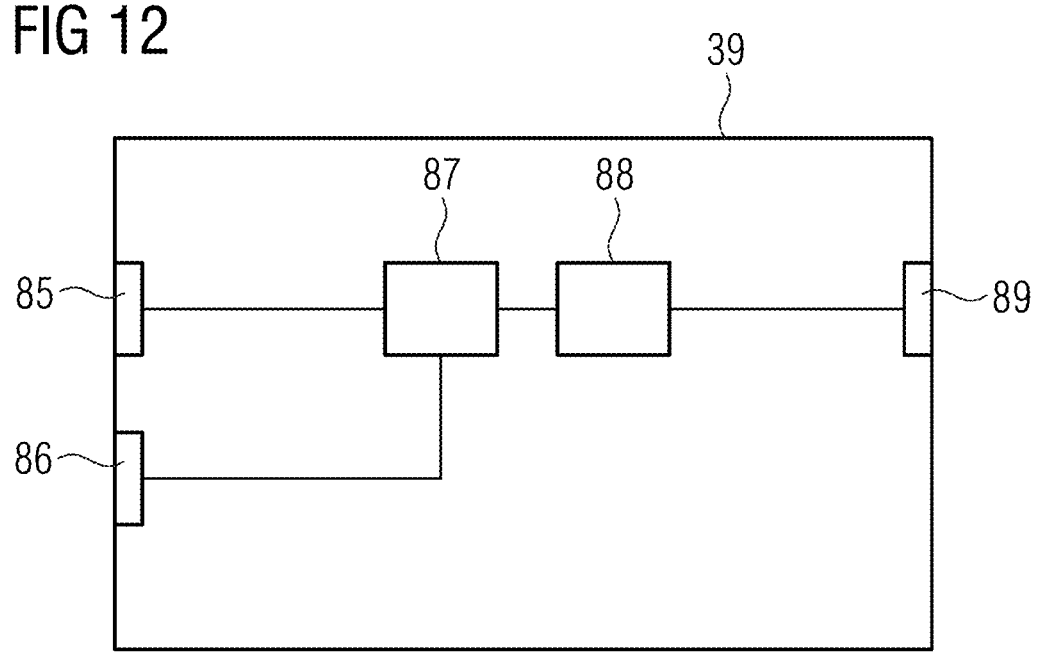
FIG. 12 shows the functional structure of a correction system in accordance with an embodiment.

The correction system 39 in accordance with FIG. 12 includes a first connection interface 85, via which the correction algorithm may be accepted from the fourth training interface 84 of the provision system 40. X-ray images to be corrected 48 may be accepted via a second application interface 86, to which the corresponding system settings (e.g., the first and second physical parameters 54, 55) are then assigned accordingly. This makes it possible, in a mask determination unit 87, to determine the refined correction mask 71, in that the trained first and second processing functions 63, 70 are applied accordingly. In a correction unit 88, the mask 71 may then be used in order to correct the x-ray image 48 to be corrected. In the correction unit 88, a denoising of the corrected x-ray image 77 may also be undertaken in addition, before the image is provided to the third application interface 89.

The correction algorithm also contains the actual correction act (e.g., the addition of mask 71 and x-ray image 48 to be corrected).

Although the invention has been illustrated and described in greater detail by the exemplary embodiments, the invention is not restricted by the disclosed examples, and other variations may be derived herefrom by the person skilled in the art without departing from the scope of protection of the invention.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method that is computer-implemented and is for provision of a correction algorithm for an x-ray image that has been recorded with an x-ray source emitting an x-ray radiation field, a filter device spatially modulating an x-ray radiation dose, and an x-ray detector, wherein the correction algorithm comprises a trained first processing function configured, from first input data that comprises at least one first physical parameter describing the x-ray radiation field, a measurement, or the x-ray radiation field and the measurement, and at least one second physical parameter describing the spatial modulation of the filter device, to determine first output data that comprises a mask for brightness compensation with regard to the spatial modulation of the filter device in the x-ray image, the method comprising:

providing first training data comprising first training datasets each with a mask, wherein each of the first training datasets is assigned the at least one first physical parameter and the at least one second physical parameter of the first input data assigned for determining the mask, providing an autoencoder for masks, wherein the autoencoder has an encoder for determining a latent space representation of the mask and a decoder for determining a comparison mask from the latent space representation;

training the autoencoder using the first training data;

determining an assignment rule between the at least one first physical parameter and the at least one second physical parameter of the first input data, which are assigned to the first training datasets, and the latent space representations of the masks of the respective first training dataset; and providing the trained first processing function as a combination of the assignment rule and the trained decoder.

2. The method of claim 1, wherein the filter is a region of interest (ROI) filter.

3. The method of claim 1, wherein:
a larger number of latent space parameters of the latent space representation than physical parameters of the first input data are used;
3 to 30 physical parameters of the first input data, 3 to 30 latent space parameters of the latent space representation, or a combination thereof are used;
the method further comprises determining at least one functional relationship at least partly by fitting, interpolation, extrapolation, or any combination thereof; or
any combination thereof.

4. The method of claim 1, wherein:
the at least one first physical parameter comprises:
a tube voltage of the x-ray source;
a tube current of the x-ray source;
a pre-filter parameter, an aperture parameter, or the pre-filter parameter and the aperture parameter;
a distance of the x-ray source to the x-ray detector;
a distance of the x-ray source to the filter device;
a distance of the filter device from the x-ray detector;
a pulse length of an x-ray pulse creating the x-ray radiation field;
a number of x-ray pulses since a beginning of a recording of a series of x-ray images;
at least one focal parameter describing a geometry of a focus point;
a zoom of the x-ray detector;
an orientation of the x-ray detector;
a frame rate of the x-ray detector; or
any combination thereof, and
the at least one second physical parameter comprises:
a material of the filter device;
at least one filter thickness parameter describing a filter thickness course;
at least one change over time of time parameters describing the spatial modulation; or
any combination.

5. The method of claim 1, wherein the first training datasets are determined from x-ray images recorded with and without the filter device.

6. The method of claim 1, wherein the correction algorithm further comprises a second processing function downstream of the first trained processing function for refining the mask determined by the first processing function, wherein the second processing function has a generator network that uses as second input data an x-ray image, for which a refined mask is to be determined, and a mask to be refined determined using the trained first processing function for the physical parameters of the first input data of the x-ray image of the second input data,
wherein for training of the second processing function, the method further comprises:
providing second training data comprising x-ray images of an object recorded with and without the filter device with assigned physical parameters of the first input data;
providing a discriminator network for discriminating between real x-ray images recorded without the filter device and x-ray images corrected using the refined mask obtained as second output data for completion of a generative adversarial network;
for training the generator network and the discriminator network, using an output of the discriminator network, by comparison of a corrected x-ray image of a second training dataset with the x-ray image, recorded without the filter device, of the second training dataset for fitting the generator network and the discriminator network; and
providing the correction algorithm comprising a combination of the trained first processing function and the trained second processing function.

7. The method as claimed in claim 6, further comprising receiving, by the generator network, at least during training of the generator network, as further second input data, at least one boundary condition restricting second output data of the generator network.

8. The method of claim 7, wherein the at least one boundary condition comprises:
a boundary condition restricting a deviation of the refined mask from the mask to be refined, a space of a possible mask to be refined, or a combination thereof;
a boundary condition ensuring a smoothness of the refined mask;
a boundary condition restricting a type of arithmetical operations for obtaining the refined mask from the mask to be refined; or
any combination thereof.

9. The method of claim 6, wherein the x-ray images are logarithmically transformed before being used as the second input data, the second training data, or the second input data and the second training data.

10. A method that is computer-implemented and is for correction of an x-ray image that was recorded with an x-ray source emitting an x-ray radiation field, a filter device spatially modulating an x-ray radiation dose, and an x-ray detector, using a correction algorithm, the method comprising:
providing the correction algorithm, wherein the correction algorithm comprises a trained first processing function configured, from first input data that comprises at least one first physical parameter describing the x-ray radiation field, a measurement, or the x-ray radiation field and the measurement, and at least one second physical parameter describing the spatial modulation of the filter device, to determine first output data that comprises a mask for brightness compensation with regard to the spatial modulation of the filter device in the x-ray image, the providing of the correction algorithm comprising:
providing first training data comprising first training datasets each with a mask, wherein each of the first training datasets is assigned the at least one first physical parameter and the at least one second physical parameter of the first input data assigned for determining the mask,
providing an autoencoder for masks, wherein the autoencoder has an encoder for determining a latent space representation of the mask and a decoder for determining a comparison mask from the latent space representation;
training the autoencoder using the first training data;
determining an assignment rule between the at least one first physical parameter and the at least one second physical parameter of the first input data, which are assigned to the first training datasets, and the latent space representations of the masks of the respective first training dataset; and
providing the trained first processing function as a combination of the assignment rule and the trained decoder, wherein the correction algorithm further comprises a second processing function downstream of the first trained processing function for refining the mask determined by the first processing function, wherein the second processing function has a generator network that uses as second input data an x-ray image, for which a refined mask is to be determined, and a mask to be refined determined using the trained first processing function for the physical parameters of the first input data of the x-ray image of the second input data;

for training of the second processing function:
providing second training data comprising x-ray images of an object recorded with and without the filter device with assigned physical parameters of the first input data;
providing a discriminator network for discriminating between real x-ray images recorded without the filter device and x-ray images corrected using the refined mask obtained as second output data for completion of a generative adversarial network; and
for training the generator network and the discriminator network, using an output of the discriminator network, by comparison of a corrected x-ray image of a second training dataset with the x-ray image, recorded without the filter device, of the second training dataset for fitting the generator network and the discriminator network; and
providing the correction algorithm comprising a combination of the trained first processing function and the trained second processing function;
determining the refined mask using the correction algorithm from at least the first input data assigned to the x-ray image to be corrected; and
using the refined mask for correction of the x-ray image to be corrected.

11. The method of claim 10, further comprising applying a denoising method to the corrected x-ray image.

12. A system for provision of a correction algorithm for an x-ray image that was recorded with an x-ray source configured to emit an x-ray radiation field, a filter device configured to spatially modulate an x-ray radiation dose, and an x-ray detector, wherein the correction algorithm comprises a trained first processing function that, from first input data that comprises at least one first physical parameter describing the x-ray radiation field, a measurement, or the x-ray radiation field and the measurement, and at least one second physical parameter describing the spatial modulation of the filter device, is configured to determine first output data that comprises a mask for brightness compensation with regard to the spatial modulation of the filter device in the x-ray image, the system comprising:

a first training interface configured to provide first training data, the first training data comprising first training datasets each with a mask, wherein the at least one first physical parameter and the at least one second physical parameter of the first input data assigned for determining the mask are assigned to each first training dataset;
a first training unit configured to train an autoencoder for masks, wherein the autoencoder has an encoder configured to determine a latent space representation of the mask and a decoder configured to determine a comparison mask from the latent space representation, using the first training data;
a rule determination unit configured to determine an assignment rule between the at least one first physical parameter and the at least one second physical parameter of the first input data, which is assigned to the first training datasets, and the latent space representations of the masks of the respective first training dataset; and
a second training interface configured to provide the trained first processing function as a combination of the assignment rule and the trained decoder.

13. A system for correction of an x-ray image that was recorded with an x-ray source configured to emit an x-ray radiation field, a filter device configured to spatially modulate an x-ray radiation dose, and an x-ray detector, the system comprising:

a first application interface configured to accept a correction algorithm provided from a system for provision of a correction algorithm for an x-ray image that was recorded with an x-ray source configured to emit an x-ray radiation field, a filter device configured to spatially modulate an x-ray radiation dose, and an x-ray detector, wherein the correction algorithm comprises a trained first processing function that, from first input data that comprises at least one first physical parameter describing the x-ray radiation field, a measurement, or the x-ray radiation field and the measurement, and at least one second physical parameter describing the spatial modulation of the filter device, is configured to determine first output data that comprises a mask for brightness compensation with regard to the spatial modulation of the filter device in the x-ray image, the system for provision of the correction algorithm comprising:

a first training interface configured to provide first training data, the first training data comprising first training datasets each with a mask, wherein the at least one first physical parameter and the at least one second physical parameter of the first input data assigned for determining the mask are assigned to each first training dataset;
a first training unit configured to train an autoencoder for masks, wherein the autoencoder has an encoder configured to determine a latent space representation of the mask and a decoder configured to determine a comparison mask from the latent space representation, using the first training data;
a rule determination unit configured to determine an assignment rule between the at least one first physical parameter and the at least one second physical parameter of the first input data, which is assigned to the first training datasets, and the latent space representations of the masks of the respective first training dataset; and
a second training interface configured to provide the trained first processing function as a combination of the assignment rule and the trained decoder;

a second application interface configured to accept the x-ray image to be corrected along with assigned first and second physical parameters;
a mask determination unit configured to determine a refined mask using the correction algorithm from at least the first input data assigned to the x-ray image to be corrected, wherein the correction algorithm further comprises a second processing function downstream of the first trained processing function and configured to refine the mask determined by the first processing function, wherein the second processing function has a generator network configured to use as second input data an x-ray image, for which the refined mask is to be determined, and a mask to be refined determined using the trained first processing function for the physical parameters of the first input data of the x-ray image of the second input data, the determination of the refined mask comprising:
for training of the second processing function:
provision of second training data comprising x-ray images of an object recorded with and without the filter device with assigned physical parameters of the first input data;
provision of a discriminator network configured to discriminate between real x-ray images recorded without the filter device and x-ray images corrected using the refined mask obtained as second output data for completion of a generative adversarial network; and
for training the generator network and the discriminator network, use of an output of the discriminator network, by comparison of a corrected x-ray image of a second training dataset with the x-ray image, recorded without the filter device, of the second training dataset for fitting the generator network and the discriminator network; and
provision of the correction algorithm comprising a combination of the trained first processing function and the trained second processing function;
a correction unit configured to use the refined mask for correction of the x-ray image to be corrected; and
a third application interface configured to provide a corrected x-ray image.

14. An x-ray facility comprising:
an x-ray source;
an x-ray detector;
a filter facility configured to spatially modulate an x-ray radiation dose; and
a controller comprising:
a system for correction of an x-ray image that was recorded with an x-ray source configured to emit an x-ray radiation field, a filter device configured to spatially modulate an x-ray radiation dose, and an x-ray detector, the system comprising:
a first application interface configured to accept a correction algorithm provided from a system for provision of a correction algorithm for an x-ray image that was recorded with an x-ray source configured to emit an x-ray radiation field, a filter device configured to spatially modulate an x-ray radiation dose, and an x-ray detector, wherein the correction algorithm comprises a trained first processing function that, from first input data that comprises at least one first physical parameter describing the x-ray radiation field, a measurement, or the x-ray radiation field and the measurement, and at least one second physical parameter describing the spatial modulation of the filter device, is configured to determine first output data that comprises a mask for brightness compensation with regard to the spatial modulation of the filter device in the x-ray image, the system for provision of the correction algorithm comprising:
a first training interface configured to provide first training data, the first training data comprising first training datasets each with a mask, wherein the at least one first physical parameter and the at least one second physical parameter of the first input data assigned for determining the mask are assigned to each first training dataset;
a first training unit configured to train an autoencoder for masks, wherein the autoencoder has an encoder configured to determine a latent space representation of the mask and a decoder configured to determine a comparison mask from the latent space representation, using the first training data;
a rule determination unit configured to determine an assignment rule between the at least one first physical parameter and the at least one second physical parameter of the first input data, which is assigned to the first training datasets, and the latent space representations of the masks of the respective first training dataset; and
a second training interface configured to provide the trained first processing function as a combination of the assignment rule and the trained decoder;
a second application interface configured to accept the x-ray image to be corrected along with assigned first and second physical parameters;
a mask determination unit configured to determine a refined mask using the correction algorithm from at least the first input data assigned to the x-ray image to be corrected, wherein the correction algorithm further comprises a second processing function downstream of the first trained processing function and configured to refine the mask determined by the first processing function, wherein the second processing function has a generator network configured to use as second input data an x-ray image, for which the refined mask is to be determined, and a mask to be refined determined using the trained first processing function for the physical parameters of the first input data of the x-ray image of the second input data, the determination of the refined mask comprising:
for training of the second processing function:
provision of second training data comprising x-ray images of an object recorded with and without the filter device with assigned physical parameters of the first input data;
provision of a discriminator network configured to discriminate between real x-ray images recorded without the filter device and x-ray images corrected using the refined mask obtained as second output data for completion of a generative adversarial network; and
for training the generator network and the discriminator network, use of an output of the discriminator network, by comparison of a corrected x-ray image of a second training dataset with the x-ray image, recorded without the filter device, of the second training dataset for fitting the generator network and the discriminator network; and
provision of the correction algorithm comprising a combination of the trained first processing function and the trained second processing function;
a correction unit configured to use the refined mask for correction of the x-ray image to be corrected; and
a third application interface configured to provide a corrected x-ray image.

15. In a non-transitory computer-readable storage medium that stores instructions executable by a computer for provision of a correction algorithm for an x-ray image that has been recorded with an x-ray source emitting an x-ray radiation field, a filter device spatially modulating an x-ray radiation dose, and an x-ray detector, wherein the correction algorithm comprises a trained first processing function configured, from first input data that comprises at least one first physical parameter describing the x-ray radiation field, a measurement, or the x-ray radiation field and the measurement, and at least one second physical parameter describing the spatial modulation of the filter device, to determine first output data that comprises a mask for brightness compensation with regard to the spatial modulation of the filter device in the x-ray image, the instructions comprising:
- providing first training data comprising first training datasets each with a mask, wherein each of the first training datasets is assigned the at least one first physical parameter and the at least one second physical parameter of the first input data assigned for determining the mask,
- providing an autoencoder for masks, wherein the autoencoder has an encoder for determining a latent space representation of the mask and a decoder for determining a comparison mask from the latent space representation;
- training the autoencoder using the first training data;
- determining an assignment rule between the at least one first physical parameter and the at least one second physical parameter of the first input data, which are assigned to the first training datasets, and the latent space representations of the masks of the respective first training dataset; and
- providing the trained first processing function as a combination of the assignment rule and the trained decoder.

* * * * *